US012564319B2

(12) United States Patent
Zavislan et al.

(10) Patent No.: US 12,564,319 B2
(45) Date of Patent: Mar. 3, 2026

(54) METHODS AND SYSTEMS FOR QUANTITATIVE OCULAR SURFACE DIAGNOSTICS

(71) Applicant: University of Rochester, Rochester, NY (US)

(72) Inventors: James M. Zavislan, Pittsford, NY (US); Aizhong Zhang, Rochester, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 17/568,685

(22) Filed: Jan. 4, 2022

(65) Prior Publication Data

US 2022/0125300 A1     Apr. 28, 2022

Related U.S. Application Data

(62) Division of application No. 16/425,870, filed on May 29, 2019, now Pat. No. 11,246,481.

(51) Int. Cl.
*A61B 3/10*          (2006.01)
*A61B 3/107*         (2006.01)
(Continued)

(52) U.S. Cl.
CPC .............. *A61B 3/101* (2013.01); *A61B 3/102* (2013.01); *A61B 3/0008* (2013.01); *A61B 3/107* (2013.01); *A61B 3/113* (2013.01)

(58) Field of Classification Search
CPC ........... A61B 3/10; A61B 3/113; A61B 3/107; A61B 2018/00785; A61B 3/101; A61B 3/102; A61B 3/132; A61B 18/14; A61B 2018/00017; A61B 2018/00023; A61B 2018/00327; A61B 2018/00648; A61B 2018/00678; A61B 2018/00708; A61B 2018/00875; A61B 2018/00898; A61B 2018/00994; A61B 2090/065;
(Continued)

(56) References Cited

U.S. PATENT DOCUMENTS

| | | | |
|---|---|---|---|
| 9,993,151 B2 * | 6/2018 | Grenon | .................. A61B 3/101 |
| 2014/0240671 A1 | 8/2014 | Korb et al. | |
| 2015/0057701 A1 * | 2/2015 | Kelleher | ........... A61H 23/0245 |
| | | | 606/204.15 |

OTHER PUBLICATIONS

Zhang, A., et al., Dynamic Characterization of Ocular Surface with Thermography and Macroscopic Imaging Ellopsometry, Requirements for the Degree Doctor of Philosophy, University of Rochester, 2017, 353 pages.
(Continued)

*Primary Examiner* — Brandi N Thomas
(74) *Attorney, Agent, or Firm* — Hodgson Russ LLP

(57) ABSTRACT

The present disclosure provides systems and methods for characterizing thin films, such as, for example, diagnosis of dry eye syndrome, thin-film optical metrology testing, etc. The present disclosure may be embodied as a tearscope, which is sometimes referred to herein as a Macroscopic Imaging Ellipsometer (MIE) because it may be considered to be an imaging ellipsometer with, for example, a field-of-view on the order of tens of millimeters or more (i.e., macroscopic), compared with conventional imaging ellipsometers, which usually employ microscope objectives and have fields-of-view of up to several hundred microns.

9 Claims, 10 Drawing Sheets

(51) Int. Cl.
   *A61B 3/00*        (2006.01)
   *A61B 3/113*       (2006.01)

(58) Field of Classification Search
   CPC .......... A61B 2562/0219; A61B 3/0008; A61B
   5/0077; A61B 5/1114; A61B 5/0073;
   A61B 18/02; A61B 18/20; A61B 18/203;
   A61B 2017/00508; A61B 2018/00577;
   A61B 2018/00613; A61B 2018/00642;
   A61B 2018/00904; A61B 2018/20355;
   A61B 2018/20359; A61B 2560/0214;
   A61B 2560/0219; A61B 2560/0252;
   A61B 2560/0418; A61B 2562/0238;
   A61B 2562/12; A61B 3/0025; A61B
   3/0058; A61B 3/1241; A61B 3/14; A61B
   3/16; A61B 3/185; A61B 5/0002; A61B
   5/01; A61B 5/031; A61B 5/14507; A61B
   5/14532; A61B 5/14539; A61B 5/14546;
   A61B 5/1455; A61B 5/14555; A61B
   5/1486; A61B 5/18; A61B 5/412; A61B
   5/416; A61B 5/445; A61B 5/4839; A61B
   5/6814; A61B 8/06; A61B 8/56; A61F
   2009/00846; A61F 2009/00872; A61F
   2009/0088; A61F 2009/00882; A61F
   9/0079; A61F 9/00825; A61F
   2009/00853; A61F 2009/0087; A61F
   2009/00887; A61F 2009/00889; A61F
   9/0017; A61F 9/008; A61F 9/00827;
   A61F 9/00829; A61F 2009/00851; A61F
   2009/00865; A61F 2009/00878; A61F
   2009/00895; A61F 2009/00897; A61F
   9/0026; A61F 9/00802; A61F 9/00838;
   A61F 9/013; A61N 1/0456; A61N
   1/36021; A61N 1/36031; A61N 1/36034;
   A61N 2005/063; A61N 2005/0643; A61N
   2005/0648; A61N 2005/0651; A61N
   2007/0078; A61N 5/0613
   See application file for complete search history.

(56) References Cited

OTHER PUBLICATIONS

Zhang, A., et al., Multimodal imaging of ocular surface of dry eye subjects, Proceedings of SPIE, Mar. 2016, 14 pages.

* cited by examiner

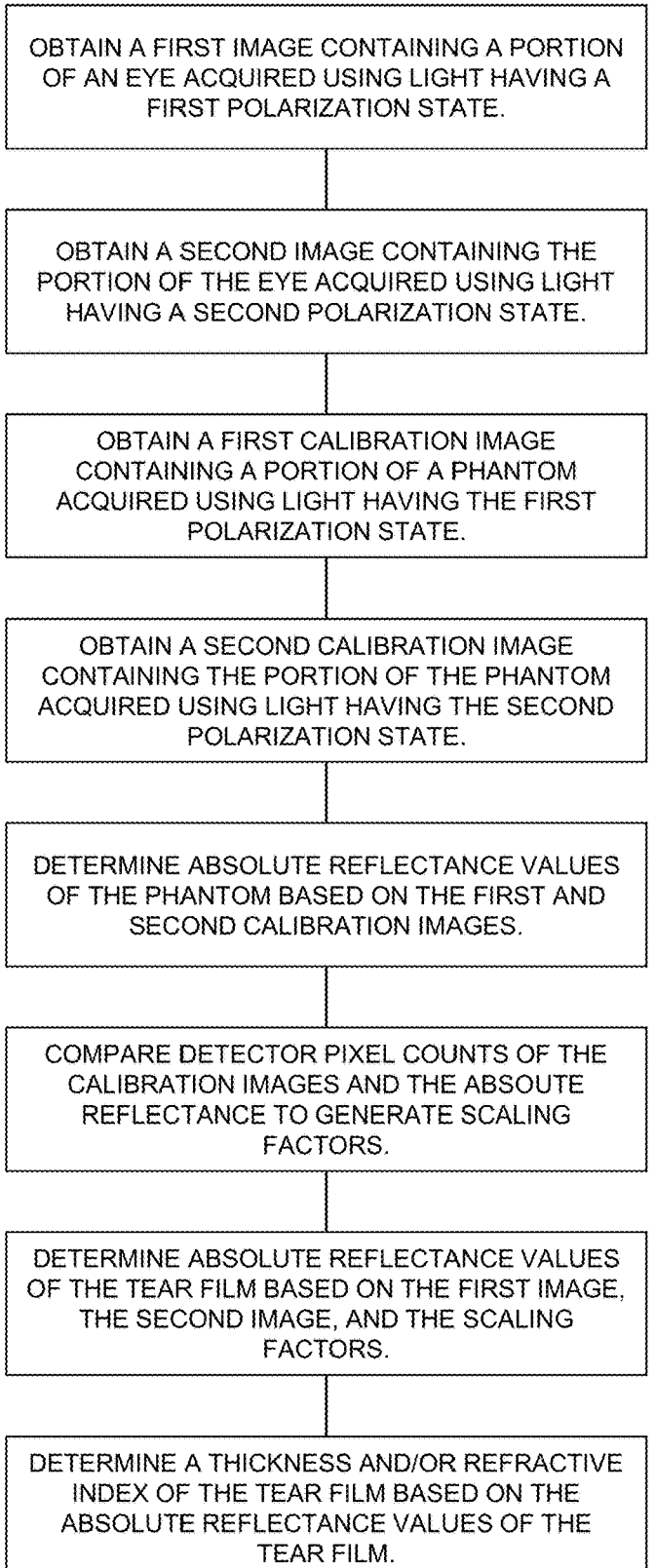

OBTAIN A FIRST IMAGE CONTAINING A PORTION OF AN EYE ACQUIRED USING LIGHT HAVING A FIRST POLARIZATION STATE.

OBTAIN A SECOND IMAGE CONTAINING THE PORTION OF THE EYE ACQUIRED USING LIGHT HAVING A SECOND POLARIZATION STATE.

OBTAIN A FIRST CALIBRATION IMAGE CONTAINING A PORTION OF A PHANTOM ACQUIRED USING LIGHT HAVING THE FIRST POLARIZATION STATE.

OBTAIN A SECOND CALIBRATION IMAGE CONTAINING THE PORTION OF THE PHANTOM ACQUIRED USING LIGHT HAVING THE SECOND POLARIZATION STATE.

DETERMINE ABSOLUTE REFLECTANCE VALUES OF THE PHANTOM BASED ON THE FIRST AND SECOND CALIBRATION IMAGES.

COMPARE DETECTOR PIXEL COUNTS OF THE CALIBRATION IMAGES AND THE ABSOUTE REFLECTANCE TO GENERATE SCALING FACTORS.

DETERMINE ABSOLUTE REFLECTANCE VALUES OF THE TEAR FILM BASED ON THE FIRST IMAGE, THE SECOND IMAGE, AND THE SCALING FACTORS.

DETERMINE A THICKNESS AND/OR REFRACTIVE INDEX OF THE TEAR FILM BASED ON THE ABSOLUTE REFLECTANCE VALUES OF THE TEAR FILM.

METHODS AND SYSTEMS FOR QUANTITATIVE OCULAR SURFACE DIAGNOSTICS

CROSS-REFERENCE TO RELATED APPLICATIONS

This application is a Division of U.S. patent application Ser. No. 16/425,870, filed May 29, 2019, the disclosure of which is incorporated herein by reference.

FIELD OF THE DISCLOSURE

The present disclosure relates to ocular health, and more particularly to devices for imaging an ocular surface.

BACKGROUND OF THE DISCLOSURE

The cornea is the anterior, transparent part of the eye. Anterior to the corneal epithelium is a moist, protective film: the tear film. The tear film forms an optical quality interface with the air and maintains the moisture of the ocular surface. Some measurements suggest that human tear film is around 3 μm thick. The tear film is composed of three layers from anterior to posterior: (1) lipid layer, (2) aqueous layer and (3) mucous layer.

Visual acuity and comfort is strongly influenced by the homogeneity and integrity of the ocular tear film. The tear film is established with each blink and after a period of time it will break, leading to a loss of visual acuity and comfort to stimulate another blink. Chronic disorders of tear film lead to a prevalent problem of dry eye syndrome. The tear film health is directly associated with the environmental conditions such as temperature, humidity and air flow rate.

Clinically, two major classes of dry eye are aqueous tear-deficient dry eye (ADDE) and evaporative dry eye (EDE), and the major type of evaporative dry eye is meibomian gland dysfunction (MGD). Clinically, hybrid types of dry eye with mixed syndromes of ADDE and EDE are not uncommon. Reduced lacrimal tear secretion from the lacrimal glands leads to ADDE. Lack of sufficient lipids secretion from meibomian glands can lead to MGD, which is the most common type of dry eye in the U.S.

Normal lipid layer thicknesses are approximately in the range of 40 to 90 nm. From the clinical measurements taken with an embodiment of a tearscope, MGD patients can have lipid layers that span from very thin (<40 nm) through to very thick (>140 nm). Some MGD patients have lipid layers that would be considered normal.

Lipid layer thickness and heterogeneity distribution correlates to the evaporation rate of the ocular surface. Lipid refractive index correlates to the chemical properties and structural orientation of the lipid. The lipids and fatty acids that make up the layer are influenced by diet and physiological state of the meibomian glands.

Clinical data from the dry eye research group at the Flaum Eye Institute, Rochester, NY, illustrates that there is a wide variation in the lipid layer thickness and heterogeneity in patients with clinically similar MGD grades, and that the clinical differential diagnosis of MGD and ADDE do not provide sensitive or specific understanding of the structure of the tear lipid layer. Thus, a careful measurement of the lipid layer thickness and refractive index may provide a detailed dynamic picture of the evolution of the lipid layer of a patient and may serve as an aid to clinically distinguish between ADDE and MGD patients, or categorize the dry eye patients into more specific subgroups.

Several methods of measuring the lipid layer thickness are available. Most of these are based on interference methods, which model the lipid layer as a single thin film on an optically massive substrate provided by the aqueous layer. These methods are further grouped into three types, namely, wavelength-dependent fringes (WDFs), thickness-dependent fringes (TDFs), and angle-dependent fringes (ADFs). Some have used a slit-lamp photometer to measure the reflectivity at two selected wavelengths, 500 and 700 nm. Others used a broad-band white source to form a color interference image to measure the lipid thickness.

However, there are limitations of these lipid layer measurement systems. Using a previously-developed system as an example, the size of a measureable region is limited to the central cornea region with a diameter of 8 mm, and only the thicknesses of several spots within the region are reported, etc. Commonly, the optical thickness of the lipid layer is inferred by the spectral reflectivity of the specular reflection. Diffuse reflection from the iris influences the overall spectrum of the light collected from eye. Because of this, only qualitative information can be obtained from corneal regions away from the pupil.

A first generation (1G) tearscope, developed by the dry eye research group at University of Rochester, uses circularly polarized illumination and orthogonal polarization analysis to separate the diffuse, depolarized scattering of the iris from the specular reflection of the cornea. This approach provides a quantitative measurement of the optical thickness of the lipid, but does not explicitly measure the refractive index and thickness of the lipid. The refractive index can be inferred from the 1G tearscope since it provides independent measurements using the RGB information from the color CCD camera. The 1G tearscope assumes a lipid refractive index of 1.451. By varying the value of the lipid and possibly including dispersion it is possible to adjust the lipid index to improve the congruence of the lipid thickness measurement. However in practice this analysis is not routinely done. Therefore, there is a need to increase the diversity of polarization states of the illumination to allow for independent thickness and index measurements.

BRIEF SUMMARY OF THE DISCLOSURE

A tearscope using macroscopic imaging ellipsometry is provided herein. The disclosed Macroscopic Imaging Ellipsometer (MIE) can simultaneously measure the thickness and refractive index of a film covering a flat or curved substrate. The MIE was tested and validated with bare BK7 and SF11 substrates, MgF$_2$ anti-reflection coated, and Al$_2$O$_3$ coated BK7 substrates with curvatures approximating the human cornea. Flat witness samples were also tested on microscope slides and Si wafers, from the same coating runs as the curved coated samples. The final results were compared with the flat witness sample results from a profilometer to measure the physical thickness of any coating, a J.A. Woollam Alpha SE ellipsometer, and a Filmetrics spectrophotometer. The calculated thicknesses accuracy of the MIE was shown to be ±10 nm and the refractive index accuracy was ±0.05. The relaxed sample alignment tolerance was ±10 mm laterally in the focal plane, and ±2.5 mm axially. The disclosed MIE has the potential to provide simultaneous measurements of lipid layer thicknesses and refractive indices, which may provide a deeper insight of tear-break-up process, and the potential for better clinical diagnosis of dry eye syndrome.

Additionally, a multimodal ocular surface imaging system that combines thermal imaging of ocular surface with macroscopic imaging ellipsometry. Thermal images measure the emissivity and temperature distributions of an object. When applied to the ocular surface, thermal imaging can provide information on evaporative cooling, tear film stability and tear film thickness. Thermal imaging has the potential to provide information about the ocular surface response to the environment and provide information to further assist in the clinical diagnosis of dry eye syndrome.

In an aspect, the present disclosure may be embodied as an apparatus for characterizing a tear film of an eye. The apparatus includes an illuminator for providing illumination light to the eye. The illuminator may include a programmable polarizer. The illuminator may include an array of liquid crystal polarization modulators. An imager is provided for receiving reflected illumination light. The imager may have at least two color channels. For example, the imager may have a red color channel, a green color channel, and a blue color channel. An analyzer is provided through which reflected illumination light is transmitted to the imager. The analyzer may be a fixed analyzer or an adjustable analyzer. For example, the analyzer may comprise a plurality of analyzers, such as, for example, a wheel of analyzers. The apparatus may further include a lens system (imaging optics) for focusing an image onto the imager. The lens system may have a field of view greater than 1 mm in linear dimension. In some embodiments, the apparatus includes a phantom having a known optical structure and a radius which is substantially the same as an eye.

The apparatus includes a controller configure to obtain from the imager: a first image containing at least a portion of the eye, wherein the first image is acquired using light having a first polarization state; a second image containing the at least a portion of the eye, wherein the second image is acquired using light having a second polarization state; a first calibration image of a phantom, wherein the first calibration image is acquired using light having the first polarization state; and a second calibration image of a phantom, wherein the second calibration image is acquired using light having the second polarization state. In some embodiments, the first and second polarization states may be caused by differently polarized illumination light. In some embodiments, the first and second polarization states are caused by the analyzer differentiating light having differing polarization.

The controller is further configured to determine reflectance values of the phantom based on the first calibration image and the second calibration image; compare measured detector pixel counts of the first and second calibration images and the reflectance values of the phantom to generate a set of scaling factors; determine reflectance values of the tear film based on the first image, the second image, and the set of scaling factors; and determine a thickness and/or refractive index of the tear film based on the reflectance values of the tear film. For example, the controller may determine a thickness and/or refractive index by way of a lookup table.

In some embodiments, the illuminator of the apparatus is further configured to emit light having a third polarization state, and the controller is further configured to obtain from the imager, a third image containing at least the portion of the eye, wherein the third image is acquired using light having the third polarization state. The controller may use the third image to remove a depolarized background signal from the first image and the second image.

The apparatus may further include an infrared imager. In such embodiments, the infrared imager is further configured to obtain from the infrared imager: a first thermal image containing the at least a portion of the eye, wherein the first thermal image is of thermal energy in a first band; and a second thermal image containing the at least a portion of the eye, wherein the second thermal image is of thermal energy in a second band different from the first band. For example, the first band may be within the range of 6-9 μm and the second band may be within the range of 9-12 μm. The controller may be configured to determine an estimated tear film thickness map based on the first thermal image and the second thermal image.

In another aspect, the present disclosure may be embodied as a method for characterizing a tear film of an eye. The method may include obtaining from an imager, a first image containing at least a portion of the eye, wherein the first image is acquired using light having a first polarization state; obtaining from the imager, a second image containing the at least a portion of the eye, wherein the second image is acquired using light having a second polarization state; obtaining from the imager, a first calibration image of a phantom, wherein the first calibration image is acquired using light having the first polarization state; obtaining from the imager, a second calibration image of a phantom, wherein the second calibration image is acquired using light having the second polarization state; determining reflectance values of the phantom based on the first calibration image and the second calibration image; comparing measured detector pixel counts of the first and second calibration images and the reflectance values of the phantom to generate a set of scaling factors; and determining reflectance values of the tear film based on the first image, the second image, and the set of scaling factors.

In some embodiments, the method further includes determining a thickness and/or a refractive index of the tear film based on the reflectance values of the eye. In some embodiments, the method further includes generating a lookup table of reflectance values for a set of tear film thicknesses and refractive indices.

In another aspect, the present disclosure may be embodied as an apparatus for measuring thermal impulse response of a tear film of an eye. The apparatus includes an infrared source configured to emit infrared energy having a known spatial pattern. The spatial pattern may be, for example, a slit, a plurality of dots, or other patterns. The infrared source may include a mask for creating the spatial pattern. The infrared source may be configured to emit long-wave and/or mid-wave infrared energy. The infrared source may comprise one or more bandpass filters. The apparatus further includes an infrared imager configured to receive infrared energy reflected by the eye; and a controller. The controller may be configured to: pulse the infrared source to emit infrared energy for a period of time; obtain from the infrared imager, at least one infrared image of at least a portion of the eye at a predetermined time after the pulse, wherein the imaged portion of the eye includes an infrared signal resulting from the spatial pattern of the infrared energy; and determine a thickness of the tear film of the eye based on the time of the obtained image and a difference between the known spatial pattern and the infrared signal in the infrared image.

In another aspect, the present disclosure may be embodied as a method for measuring a thermal impulse response of a tear film of an eye. The method includes pulsing an infrared source for a period of time, the infrared source having a known spatial pattern and configured to project the spatial pattern onto the eye; obtaining from an infrared imager, a first infrared image of at least a portion of the eye at a predetermined time after the pulse, wherein the imaged portion of the eye includes an infrared signal resulting from the spatial pattern of the infrared energy; and determining a thickness of the tear film of the eye based on the time of the first infrared image and a difference between the known spatial pattern and the infrared signal in the first infrared image. The method may further include obtaining additional infrared images of the portion of the eye at a different times after the pulse, and wherein the thickness of the tear film is determined using the first infrared image and the additional infrared images.

In another aspect, the present disclosure may be embodied as an apparatus for measuring a thickness of a tear film of an eye. The apparatus includes an infrared source configured to selectively emit infrared energy in a first range and infrared energy in a second range; an infrared imager configured to receive infrared energy reflected by the eye; and a controller. The controller may be configured to: obtain from the infrared imager, a first infrared image of at least a portion of the eye, wherein the first infrared image is acquired using infrared energy in the first range (for example, between 6.5 and 9 μm, inclusive); obtain from the infrared imager, a second infrared image of at least the portion of the eye, wherein the second infrared image is acquired using infrared energy in the second range (for example, between 9 and 12 μm, inclusive); and subtract the second image from the first image to obtain an infrared image of the tear film.

In another aspect, the present disclosure may be embodied as a method for measuring a thickness of a tear film of an eye. The method may include obtaining a first infrared image of at least a portion of the eye, wherein the first infrared image is acquired using infrared energy in a first range (for example, between 6.5 and 9 μm, inclusive); obtaining a second infrared image of at least a portion of the eye, wherein the second infrared image is acquired using infrared energy in a second range (for example, between 9 and 12 μm, inclusive); and subtracting the second image from the first image to obtain an infrared image of the tear film of the eye.

In another aspect, the present disclosure may be embodied as an apparatus for measuring a corneal topography. The apparatus may include an illuminator for providing illumination light to the eye, the illuminator configured to emit light having at least two polarization states simultaneously and wherein the illuminator varies the polarization output temporally and spatially; an imager for receiving reflected illumination light; an analyzer through which reflected illumination light is transmitted to the imager; and a controller. The controller may be configured to obtain from the imager, a plurality of images of the eye over time, wherein each image includes at least a same portion of the eye acquired with light having spatial polarization different from other images of the plurality of images; determine an edge of the spatial polarization in each image and/or local maximum and minimum positions of the spatial polarization in each image; and calculate a set of contour maps of the corneal topography of the eye, wherein each contour map of the set of contour maps is calculated using the determined local maximum and minimum positions.

In some embodiments, the controller is further configured to combine the set of contour maps to create a dynamic corneal evolution video. The apparatus may further include a set of registration markers, and the controller may be further configured to align each image of the plurality of images to accommodate eye movement. Each registration marker may be, for example, a light-emitting diode. In some embodiments, the illuminator may be configured to vary the polarization using a Placido disc.

DESCRIPTION OF THE DRAWINGS

For a fuller understanding of the nature and objects of the disclosure, reference should be made to the following detailed description taken in conjunction with the accompanying drawings, in which:

FIG. 3 is a chart of a method according to another embodiment of the present disclosure;

DETAILED DESCRIPTION OF THE DISCLOSURE

Figure 1A:
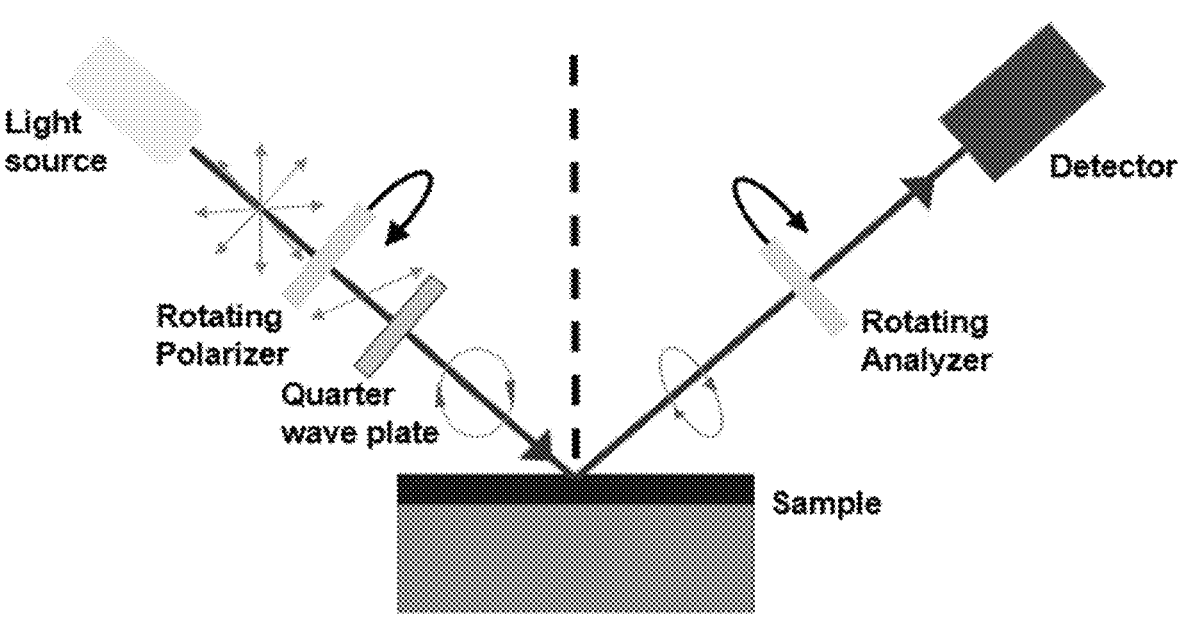
FIG. 1A is a diagram of a nulling ellipsometer.

The presently-disclosed systems and methods are useful in the characterization of thin films, such as, for example, diagnosis of dry eye syndrome, thin-film optical metrology testing, etc. For illustration only, and not intended to be limiting in any way, the systems and method will be discussed herein with respect to measuring a dynamic lipid layer distribution on an ocular surface. Dry eye syndrome is a chronic ocular disorder, and patients either cannot produce enough tears or have poor tear quality. Clinically, it is known that abnormalities in the thickness and distribution of the lipid layer correlate to symptoms of dry eye syndrome.

An object of some embodiments of the present systems and methods is to characterize the tear film of an ocular surface with both the lipid layer thicknesses and refractive indices distribution. This information could then be tested in clinical trials to potentially enhance diagnostic criteria of dry eye syndrome and objectively test various treatments, among other uses.

The present disclosure may be embodied as a tearscope, which is sometimes referred to herein as a Macroscopic Imaging Ellipsometer (MIE) because it may be considered to be an imaging ellipsometer with a field-of-view on the order of tens of millimeters or more (i.e., macroscopic), compared with conventional imaging ellipsometers, which usually employ microscope objectives and have fields-of-view of up to several hundred microns.

Conventional Ellipsometry

Ellipsometry is a method for the investigation of the properties of thin films coatings and bare surfaces. Ellipsometry is non-destructive and contactless, and it can provide in situ and real-time characterization of surfaces, interfaces, and thin films. Ellipsometry measures the change in polarization state of light before and after reflection from a coating or surface. The change in polarization state depends on the real and imaginary parts of the refractive index of the coating and substrate, the thickness of the coatings, the angle of incidence of the illumination relative to the surface normal, and the wavelength of the illumination.

Mathematically, the polarization changes after reflection off different samples are modeled by the Fresnel reflection coefficients and the interference of the light reflected from the interfaces. For an uncoated substrate, the amplitude Fresnel reflection coefficients of electric field components can be derived from Maxwell's equations and the appropriate boundary conditions at an interface. The electric field component that is polarized parallel (p polarization) to the plane of incidence, and the component polarized perpendicular to the plane of incidence (s polarization) have different refractive index and incident angle dependence. These dependence relations come from the boundary condition to ensure the tangential components of the electric fields be continuous at the interface. The electric field reflectivity coefficients between two materials, medium 0 (usually indicates air), and medium 1 (usually used to denote the coating layer, unless the sample is a bare substrate) are:

$$r_{01}^p = \frac{n_1\cos\theta_0 - n_o\cos\theta_1}{n_1\cos\theta_0 + n_o\cos\theta_1}, r_{01}^s = \frac{n_0\cos\theta_0 - n_1\cos\theta_1}{n_0\cos\theta_0 + n_1\cos\theta_1}, \quad (1)$$

where $n_0$ and $\theta_0$ are the index and angle of propagation in the incident medium 0, and $n_1$ and $\theta_1$ are the index and angle of propagation in the incident medium 1.

If the materials are absorbing, the refractive indices are complex numbers, and we can simply replace $n_j$ with the complex refractive index $N_j = n_j - i\kappa_j$, $j = 0, 1$, where $n_j$ is the real part of the refractive index, and $\kappa_j$ is the extinction coefficient. The irradiance reflectance of the two orthogonal polarization components are $\mathcal{R}^P = |r^p|^2$, and $\mathcal{R}^s = |r^s|^2$.

Similarly, the coefficients at the interface between medium 1 (usually optical coating layer) and medium 2 (usually substrate) are:

$$r_{12}^p = \frac{n_2\cos\theta_1 - n_1\cos\theta_2}{n_2\cos\theta_1 + n_1\cos\theta_2}, r_{12}^s = \frac{n_1\cos\theta_1 - n_2\cos\theta_2}{n_1\cos\theta_1 + n_2\cos\theta_2}, \quad (2)$$

where $n_2$ and $\theta_2$ are the index and angle of propagation in the incident medium 2.

If the light is incident upon a multilayer structure with layer thicknesses that are much less than the longitudinal coherence length of the illumination, the total reflected wave returning to the incident medium is the coherent summation of multiple reflected and transmitted waves.

Drude investigated the optical properties of light reflected from solids, and laid the foundation for ellipsometry with two fundamental articles published in 1889 and 1890. Using Fresnel coefficients of reflection and taking multiple reflections into account for a single optically thin layer sitting on an optically massive substrate, the ratios of the amplitude of the resultant reflected wave to the amplitude of the incident wave are given by the total reflectivity coefficients:

$$R^P = \frac{r_{01}^p + r_{12}^p e^{-i2\beta}}{1 + r_{01}^p r_{12}^p e^{-i2\beta}}, R^s = \frac{r_{01}^s + r_{12}^s e^{-i2\beta}}{1 + r_{01}^s r_{12}^s e^{-i2\beta}}, \quad (3)$$

where $\beta$ is the effective phase thickness of the layer:

$$\beta = 2\pi\frac{d}{\lambda}n_1\cos\theta_1, \text{ or } \beta = 2\pi\frac{d}{\lambda}N_1\cos\theta_1,$$

if the second medium has a complex refractive index. Note the irradiance reflectance components are now $\mathcal{R}^P = |R^p|^2$, and $\mathcal{R}^s = |R^s|^2$.

For more complicated multilayer coating structures, the total reflectivity coefficients can be calculated by using Rouard's method, which is a stepwise procedure that uses the above formula recursively starting from the bottom of the coating stack, and treats the already analyzed part as a new substrate.

In ellipsometry, two auxiliary parameters: $\Psi$ and $\Delta$ are introduced to characterize the complex ratio of the total reflectivity off the surface, $$\rho = \frac{R^p}{R^s} = \tan\Psi e^{i\Delta}, \quad (4)$$

where tan $$\Psi = \frac{|R^p|}{|R^s|},$$

and $\Delta$ is the relative phase difference between the p and s polarization components. The angle $\Psi$ is usually restricted between $0°\sim90°$, whereas $\Delta$ can take any value over $0°\sim360°$.

In a typical implementation of ellipsometry, a flat sample is illuminated with a narrow, effectively collimated beam of monochromatic light of known polarization, at a known angle of incidence. If a white light source is used, usually there will be a spectrometer to separate different wavelengths in the detection arm. Using a rotating analyzer, or adjusting both the polarizer and the analyzer, or introducing the adjustable optical compensators in the light pathways, the change in polarization after reflection from the sample can be measured. From this polarization change, $\Psi$ and $\Delta$ can be extracted, and from each $\Psi$ and $\Delta$ measurement, the two optical parameters (the coating thickness and refractive index) of the sample can be calculated. Making measurements with different wavelengths or angles of incidence, allows for extraction of additional optical parameters. Assuming there are sufficient independent measurements, and comparing these measurements to theoretical models of thin film reflection, one can determine: (1) material optical constant n and $\kappa$, (2) material dispersion, and (3) layer thickness.

Figure 1B:
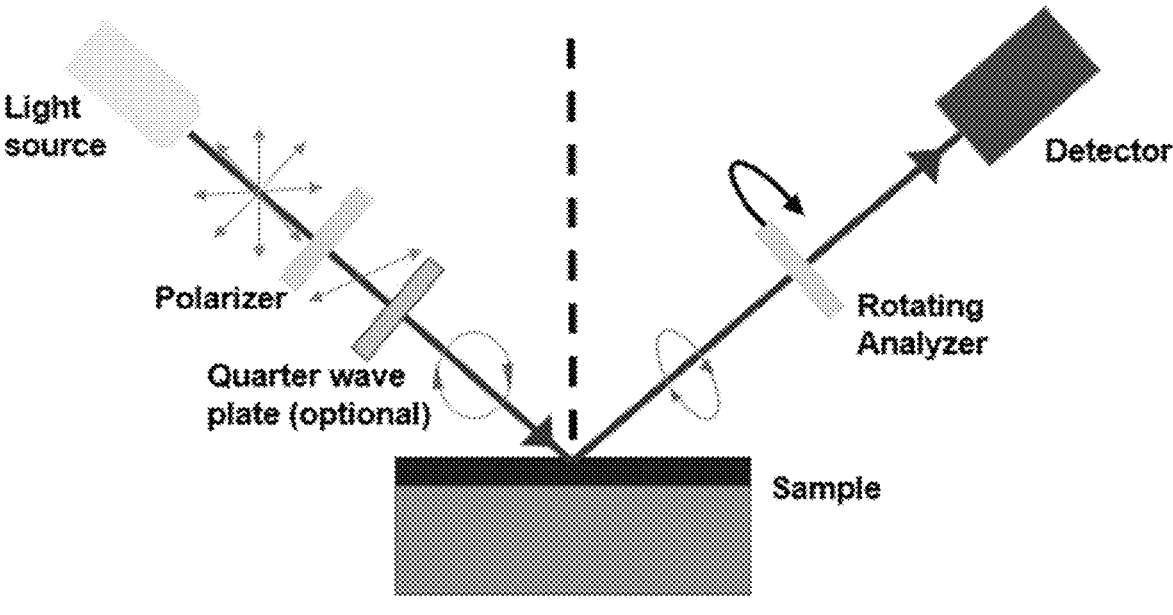
FIG. 1B is a diagram of a rotating analyzer ellipsometer.

There are several basic designs of ellipsometers in general use. The differences between the various instruments are mostly due to the choice of polarizer and analyzer systems, and the light sources. Common implementations include nulling ellipsometers, rotating analyzer, photo-elastic modulator ellipsometers, and phase-shift imaging ellipsometers. FIGS. 1A and 1B show two types of common ellipsometers: (a) a null ellipsometer, in which both the polarizer and the analyzer rotate alternatively until the null is achieve in the detector (FIG. 1A); and (b) a rotating analyzer ellipsometer, where only the analyzer rotates (FIG. 1B).

Imaging Ellipsometry

Imaging ellipsometry is a branch of ellipsometry that uses an imager (camera, etc.) as a detector. It can be used for quantification and visualization of the thickness distribution of thin transparent layers on substrates. Imaging ellipsometry may combine standard single-beam ellipsometry with microscopy, and the field of view of the imaging objective generally sets the field of view of the imaging ellipsometer. The main advantage of imaging ellipsometry is that every point on a surface is independently measured at the same time based on the optical resolution of the imaging system. In some setups, a high spatial resolution on the order of micrometers (laterally) and sub-nanometers (thickness) can be achieved.

Each region of the surface introduces a different $\Psi$ and $\Delta$, and from the measured $\Psi$ and $\Delta$ map over the region of interest, the thickness and refractive index map over the same region can be reconstructed. However, there is a tradeoff between the lateral resolution that requires a diversity of illumination angles and the polarization purity of the reflected light. Thus, it is not possible to simultaneously achieve both high lateral resolution and high ellipsometric accuracy.

Macroscopic Imaging Ellipsometer

Figure 2:
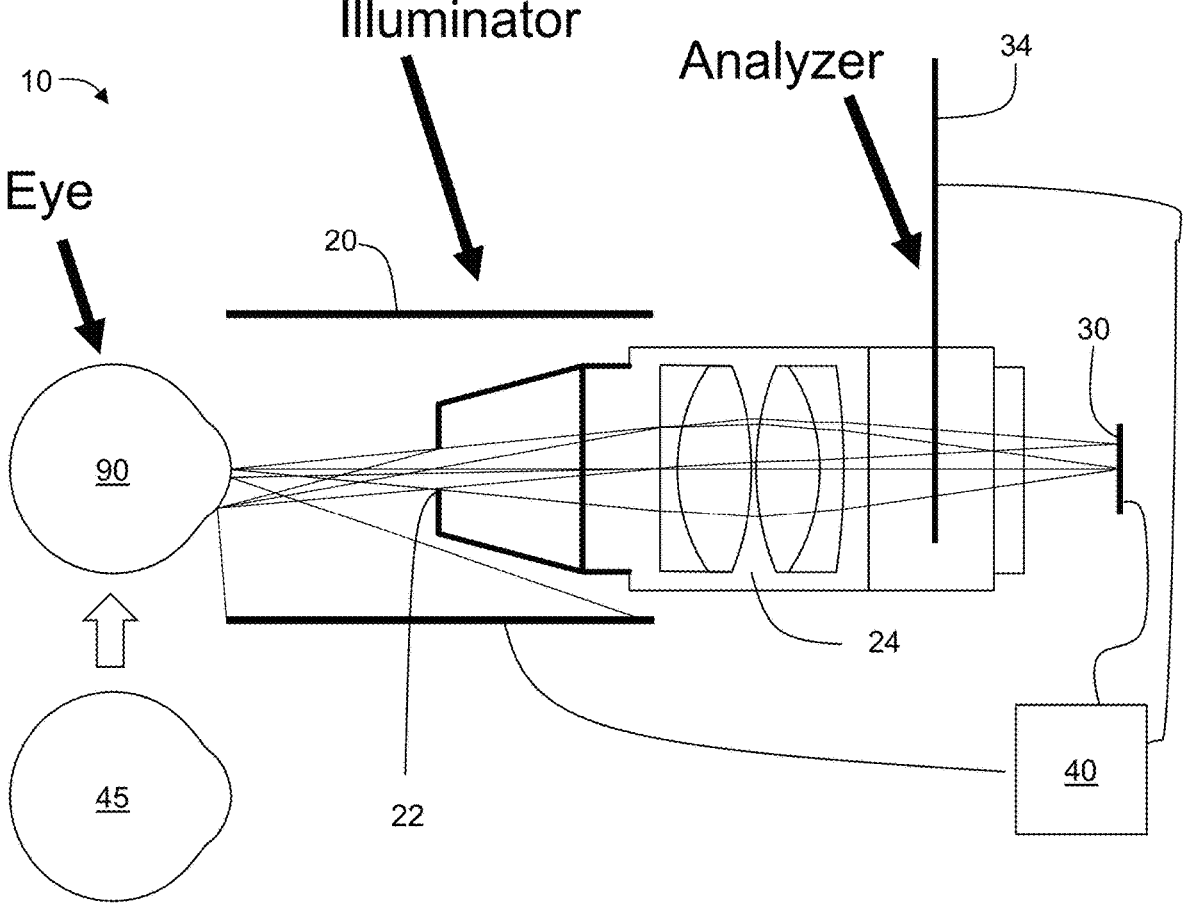
FIG. 2 is a diagram of a macroscopic imaging ellipsometer (MIE) according to an embodiment of the present disclosure.
Figure 4:
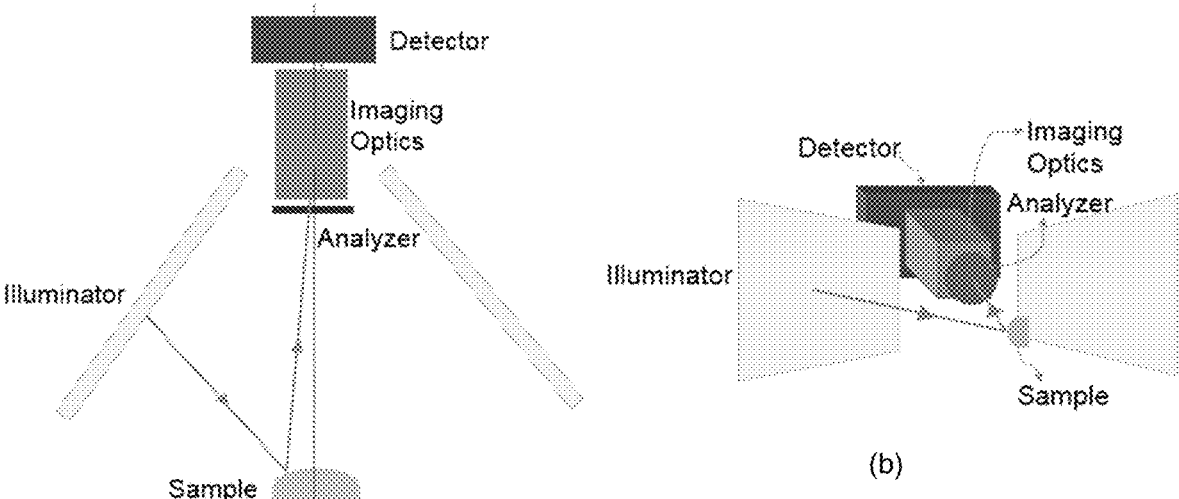
FIG. 4 is a diagram of an MIE according to another embodiment (1. Left: Top-down view. Right: side view)

FIG. 2 shows a schematic of an embodiment of the presently-disclosed MIE—the tearscope 10. It illustrates an exemplary configuration used for the tests described herein. Stepwise polarization analysis through all the polarization elements in a system including the sample is used to derive the output irradiance as a function of input polarization state and sample refractive index and thickness. In a sample having a thin-film coating on a substrate, the thickness and refractive index of the coating and the refractive index of the substrate determine the reflection matrix.

Of particular interest are samples that are thick and have a scattering layer separated from the interface to be characterized. An example is the eye, where the ocular surface layer is separated from the iris. Light illuminating the ocular surface also is transmitted to the iris. Light scattered from the iris can be included with the light reflected of the ocular surface. It is possible by configuring the MIE to distinguish light reflected from a diffuse scattering surface from the light reflected of the interface to be characterized.

Also of interest is the ability to compensate for the spatial variation of illumination radiance and provide for reduced tolerance in polarization accuracy in the illumination. It is common for area illuminators to have variations in brightness (radiance). For example an illuminator may use discrete white light emitting diodes (LED) illuminating a diffusing structure such as white plastic that is covered by polarizing film. While the diffusing structure can redistribute the light from the LEDs to make it more spatially uniform, it is difficult to make an area illuminator completely uniform. The spatial non-uniformities of the area illuminator can influence the analysis of the reflectance of a sample since knowledge of the spatial uniformity of the illuminator is needed to determine what parts of the image irradiance variations are due to spatial reflectance variations of the sample or spatial radiance variations.

The MIE may be configured to operate with reduced illuminator uniformity requirements by configuring the illuminator to provide multiple, different polarization states where it is assumed the change in radiance between polarization states is known or is sufficiently low as to not affect the accuracy of the system. This configuration is referred to as effective reflectance imaging ellipsometry (ERIE). In its operation, the illuminator may be imaged after reflecting off the unknown sample and images are captured for each of the polarization states of the illuminator. Because the change in radiance between the polarization states is known it is possible to process the image irradiance that includes the polarization reflectivities of the sample to extract the effect of the sample independent of the spatial radiance uniformity of the illuminator.

The MIE may be configured to operate with reduced illuminator uniformity requirements by imaging a reflectance standard or phantom with geometry similar to the sample being measured. For example, a 12 mm diameter curved glass substrate with a front surface radius of curvature of 7.8 mm can serve as a reflectance standard for characterizing the ocular tear film. In this configuration, the phantom is imaged under the illumination of all the desired polarization states either before or after imaging the sample or both before and after imaging the sample. The images from the phantom and sample for each polarization illumination states are scaled and aligned so that it is possible to divide the detected sample pixel intensities by the detected phantom pixel intensities pixel by pixel so to normalize the spatial variations of the illuminator. This normalized measurement can then by multiplied by the theoretical reflectance at each point on the phantom for the illumination and imaging geometry to provide an absolute reflectance of the sample for this illumination polarization. This configuration is referred to as absolute reflectance imaging ellipsometry (ARIE).

In either effective or absolute reflectance imaging ellipsometry the polarization state of the illuminator can be configured to be uniform over the illumination area or it can be configured to be structured so that different regions would have different but specified polarization states.

With reference to FIG. 2, in a first aspect, an apparatus 10 for characterizing a tear film of an eye 90 is provided. The apparatus 10 includes an illuminator 20 for providing illumination light to the eye 90. The illuminator 20 may be configured to emit light having one or more polarization states, such as, for example, a first polarization state and light having a second polarization state.

The tearscope 10 further includes an imager 30 and imaging optics 24 with an entrance pupil 22. In some embodiments, the entrance pupil 22 is close to the eye to increase the diversity of angles of incidence of the chief ray across the eye. The entrance pupil 22 may coincide with a physical aperture stop or may be an image of a physical aperture stop within the imaging optics 24. The imager 30 may include a charge-coupled device (CCD) sensor, a complementary metal oxide semiconductor (CMOS) sensor, etc. In some embodiments, the imager may include imaging optics, and entrance pupil, etc. The imager 30 is configured to receive light reflected from the eye 90—i.e., as the eye 90 is illuminated by light from illuminator 20. An analyzer 34 is provided and arranged such that reflected illumination light is transmitted from the eye 90 to the imager 30 through the analyzer 34. Analyzer 34 can be configured to be either fixed or adjustable. When configured to be fixed, analyzer 34 will allow the passage of one polarization state to the sensor 30. When configured to be adjustable, the analyzer 34 can be switched to allow the sequential passage of two or more polarization states to the sensor.

A controller 40 is in communication with the imager 30. The controller 40 is configured to obtain a first image containing at least a portion of the eye 90. The first image is acquired using light having the first polarization state. The first image is obtained from the imager 30. For example, the first image may be obtained by the imager 30 using illumination light having the first polarization state. In another example, the analyzer 34 may be configured to differentiate (i.e., and pass) light having the first polarization state. The controller 40 further obtains from the imager 30 a second image containing at least a portion of the eye 90. The second image is acquired using light having the second polarization state. Here again, the second polarization state may be provided based on illumination light (i.e., differently polarized light provided by the illuminator) or based on differentiate by the analyzer.

The controller 40 also obtains a first calibration image of a phantom 45. The first image is acquired using light having the first polarization state. The controller 40 further obtains from the imager 30 a second calibration image of the phantom 45, where the second image is acquired using light having the second polarization state. The calibration images of the phantom may be taken before or after or before and after the capture of the images of the eye.

The controller 40 is further configured to determine reflectance values of the phantom 45 based on the first calibration image and the second calibration image. The controller 40 generates a set of scaling factors by comparing measured detector pixel counts of the first and second calibration images and the reflectance values of the phantom 45. Using the first image, the second image, and the set of scaling factors, the reflectance values of the tear film are determined. The controller 40 determines a thickness and/or refractive index of the tear film based on the reflectance values of the tear film. For example, the controller 40 may access a lookup table to determine the thickness and/or refractive index of the tear film.

In some embodiments, the controller 40 may be further configured to obtain, from the imager 30, a third image containing at least a portion of the eye 90 and where the third image is acquired using light having the third polarization state. For example, the illuminator 20 of the tearscope 10 may be further configured to emit light having the third polarization state. In another example, the analyzer 34 may be configured to differentiate the third polarization state. The third image is used to remove a depolarized background signal from the first image and the second image.

In some embodiments, the polarization state emitted from illuminator 20 is fixed and the analyzer 34 is configurable to measure two or more polarization states. In these embodiments, the controller 40 is again in communication with the imager 30. The controller 40 is configured to obtain a first image containing at least a portion of the eye 90 or phantom 45. The first image is acquired using illumination light having the first polarization state. The first image is obtained by passing light through analyzer 34 configured to transmit a first analyzed polarization state to the imager 30. The controller 40 further obtains from the imager 30 a second image is obtained by passing light through analyzer 34 configured to transmit a second analyzed polarization state to the imager 30 containing at least a portion of the eye 90 or phantom 45. Additional images can be obtained by configuring analyzer 34 to pass third analyzed polarization states to the imager 30 of either the eye 90 or phantom 45.

In some embodiments, the polarization state emitted from illuminator 20 is configurable between two or more illumination polarization states and the analyzer is configured to measure two or more polarization states. In such embodiments, the MIE 10 obtains images of the eye or phantom by illuminating with one or more polarized illumination and detecting light reflected from either the eye 90 or phantom 45 through analyzer 34 configured to pass light of one or more analyzed polarization states to sensor 30. Controller 40 may process the eye images to determine a thickness and/or refractive index of the tear film based on the effective reflectance values of the tear film. Controller 40 may process the eye images and phantom images to determine a thickness and/or refractive index of the tear film based on the absolute reflectance values of the tear film.

Figure 5:
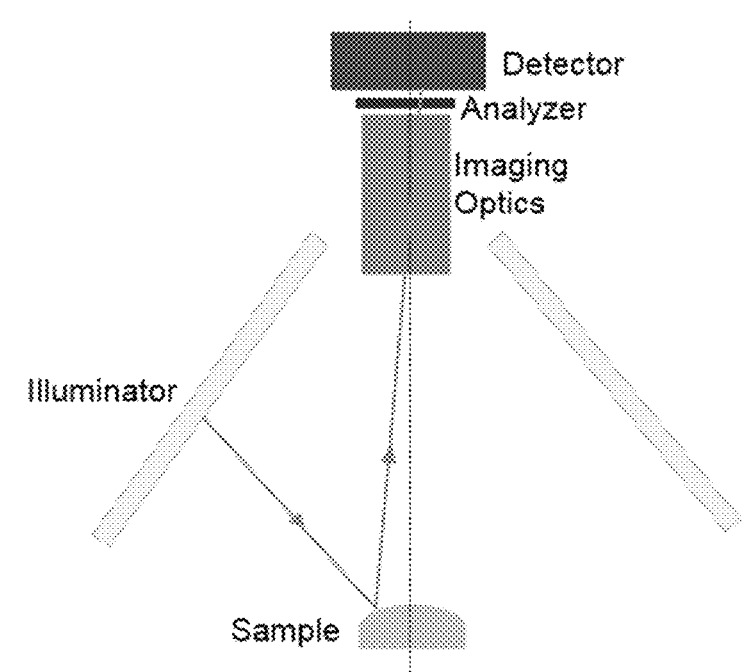
FIG. 5 is a diagram an MIE according to another embodiment.

In some embodiments of the MIE, the analyzer is located after imaging optics (see, e.g., FIG. 5). In each case, the analyzer is located at a position before light impinges the detector. Where birefringence of the imaging optics can be ignored, the same calibration and calculation process could be applied to either configuration. Even if the imaging optics have some birefringence, the polarization characterization uncertainty and/or the errors caused by the birefringence of the imaging optics may be calibrated out with the use of the calibration phantom as described above.

Figure 6:
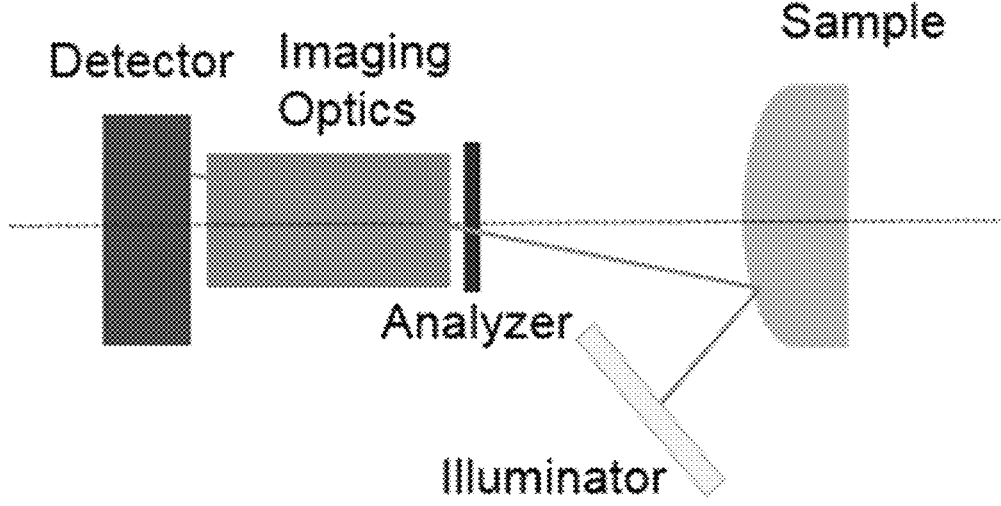
FIG. 6 is a diagram an MIE according to another embodiment.

In another exemplary of an MIE, a small LCD modulator, such as a modified liquid crystal microdisplay (e.g., a backlit LCD display without the typical front polarizing element), is used as the illumination source, positioned to be tilted and inferior to the human cornea when used with a subject (see, e.g., FIG. 6). An imager with an analyzer, such as a fixed analyzer, in front of it can be used to collect light reflected from the tear film.

Another exemplary embodiment of an MIE has three different analyzers in a rotating analyzer wheel. For example, instead of just using left and right hand circularly polarizers, left and right hand circularly polarizers and an additional +45° linear polarizer could be used. The stepwise polarization analysis described above is adjusted accordingly, but similar to other embodiments, a lookup table of effective reflectance may be used to retrieve the thickness and refractive index of thin film coatings following the ERIE method.

In some embodiments, a Placido disk corneal topographer is used to assess the tear film. This instrument has an illuminator having concentric rings of differently-structured light with a central port to view the reflection of the rings off the ocular surface. The location of the images of the ring edges after reflecting off the ocular surface is related to the local slope of the ocular surface. Clinically, these instruments measure the curvature of the cornea and also the stability of the tear layer by analyzing the spacing and distortions of the images of the rings.

The polarized light emitted from the illuminator may be spatially structured in the MIE systems to allow for the system to simultaneously operate as both a Placido disk corneal topographer as well a measure the lipid thickness or lipid thickness and lipid index. In some embodiments of the MIE system, the illuminator includes a spatially-structured polarized light emitter. A backlit LCD display operates in this mode if the front polarizing element is either not installed at the time of assembly or removed.

Figure 13:
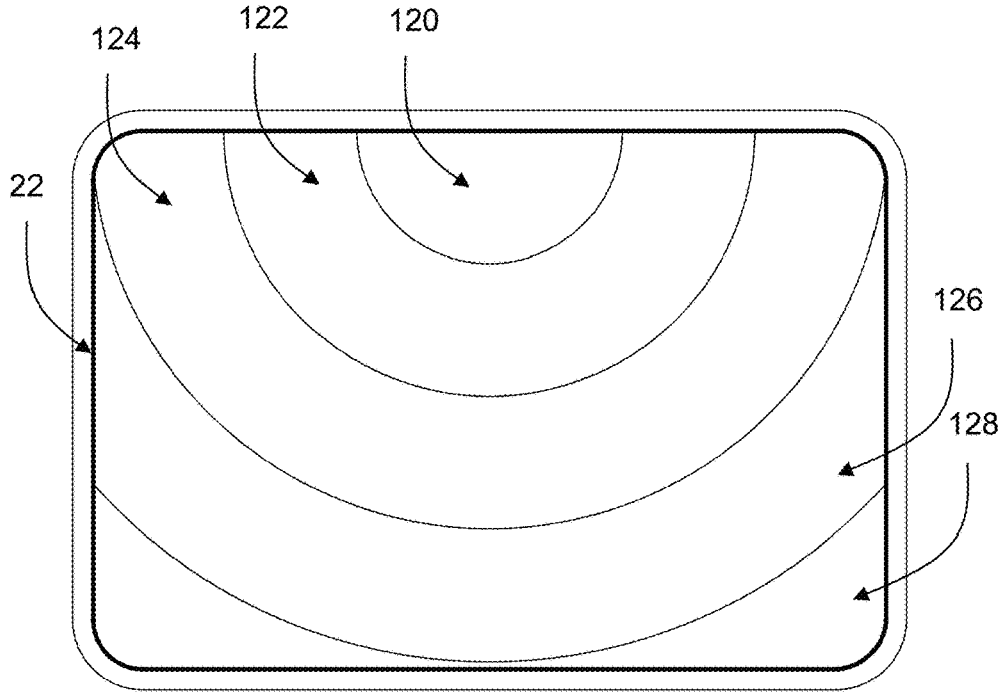
FIG. 13 is en face view of a polarized illuminator with spatially varying polarization states.
Figure 14:
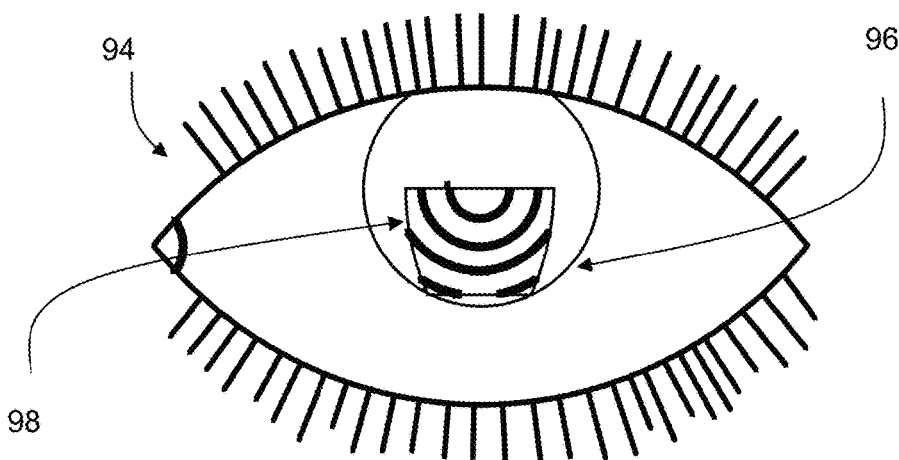
FIG. 14 is a view of the eye illuminated by a spatially varying polarized illuminator through a polarization analyzer.

As described previously, ARIE or ERIE modes of operation can be achieved by illuminating the ocular surface with two or more polarization states. Uniformly polarized illumination states can be sequentially presented to the ocular surface and images captured by passing the reflected light from the ocular surface or phantom through a polarization analyzer to allow for the calculation of the lipid thickness or lipid thickness and index depending on the number of states used. The polarized illumination can also be spatially structured with two or more differently polarized states being emitted at different positions on the illuminator. This is illustrated in FIG. 13. On illuminator 21 these polarized illumination states can be organized as concentric rings 120, 122, 124, 126, 128 so that after reflection from the ocular surface and observation through an analyzer, the images will appear as concentric rings of different irradiance on the ocular surface as illustrated in FIG. 14. The eye 94 under examination is illuminated by illuminator 21. The ocular surface of the cornea 96 reflects the light toward the imager 36. The concentric areas of the illuminator, 120, 122, 124, 126, 128, will appear after polarization analysis as rings on the ocular surface 98. The shape of the edges of the rings will depend on the local slope of the ocular surface. Thus, by analyzing the shape of the edges of the rings visible in the polarized image of the ocular surface the local slope of the ocular surface can be inferred by known Placido disk analysis techniques.

The irradiance of the image within each ring will depend on the lipid thickness and index, as described by the MIE operation: the local angle of incidence, the center wavelength of the detected light, polarization state of the illumination and the polarization analyzer state. In order to extract the lipid thickness or lipid thickness and lipid index, two or more polarized illumination states must be presented. This can be done by structuring the illuminator with concentric rings of two polarization states using controller 42 or 44 and alternating the polarization states between the rings as each set of images is captured through the polarization analyzer. Referring back to FIG. 13, regions 120, 124 and 128 would each emit the same first polarization state. Regions 122 and 126 would each emit the same second polarization state. Edge information is available within each image to measure topographic changes in the ocular surface including the onset of tear break up, and lipid thickness at any illuminated part of the ocular surface can be measured after capturing two images (one for each illumination polarization) through the polarization analyzer.

This technique can be extended to three different polarized illumination states by configuring the illuminator to have repeating concentric rings each emitting light from one of the three differently polarized states. In operation the illuminator would be configured by controller 42 or 44 so that each ring area of the illuminator would sequentially present each of the polarized emissions, but for each configuration adjacent ring areas would present a different polarization state. For example in FIG. 13, regions 120 and 126 would be configured to each emit the same first polarization state. Regions 122 and 128 would be configured each emit the same second polarization state. Region 124 would be configured to emit a third polarization state. A first image would be captured with the screen so configured. Next, regions 120 and 126 would be configured to each emit the same second polarization state. Regions 122 and 128 would be configured to each emit the same third polarization state. Region 124 would be configured to emit the first polarization state. A second image would be captured with the screen so configured. Next, regions 120 and 126 would be configured to each emit the same third polarization state. Regions 122 and 128 would be configured to each emit the same first polarization state. Region 124 would be configured to emit the second polarization state. A third image would be captured with the screen so configured. Edge information can be calculated by controller 42 or 44 from each of the images to measure topographic changes in the ocular surface. For each pixel in image of the screen 21 as it is reflected of the tear layer, the three images captured can be processed by controller 42 or 44 using the ERIE algorithm to extract the lipid thickness and lipid index.

By analogous extension, the case of three polarized illuminations, four or more polarized illuminations can be configured to be emitted from the illuminator 21 or any other illuminator configuration used by the MIE. The number of rings can be increased, but the width of the rings on the illuminator should be large enough so that the images of the ring can be resolved within the captured images.

The order of the polarization states of the rings can be changed so that the average irradiance of the captured images would follow a cosine or sine radial variation from the center of the eye. By configuring the polarization states in this way, the surface topology can be extracted for all points of the image and not just the edges, if the spatial phase of the pattern is varied by $\pi/3$, $\pi$ and $5\pi/3$ between successive images. This allows for the surface slope for each point to be calculated by controller 42 or 44 using the three image phase shifting interferogram analysis technique.

The surface slope S(i,j) using this technique is $$S(i, j) = \tan^{-1}\left\{ \frac{\sqrt{3}\,[I(i, j; 5\pi/3) - I(i, j; \pi/3)]}{I(i, j; 5\pi/3) + I(i, j; \pi/3) - 2I(i, j; \pi)} \right\},$$

where $I(i,j;\pi/3)$, $I(i,j;\pi)$ and $I(i,j;5\pi/3)$ are the image pixel values for either the individual red, green or blue channels for each of the shifted polarization patterns that make up the nominal cosine or sine pattern. The (i,j) pixel is within the image of the illuminator after reflection off the ocular surface. Alternatively, the red, green and blue pixel channels could be summed and these aggregated values be used for each pixel locations. Four-image and five-image reconstruction algorithms are also known and could be used if the ERIE or ARIE reconstruction required more than three different polarizations.

The corneal topography mode of operation can also use the corneal phantom to calibrate and correct the measured surface slope for a given polarization distribution on the illuminator. Also using the calibration phantom, the shape of the rings on the illuminator can be varied under software control of controllers 42 or 44 so to make the image of the rings of the phantom surface appear to be round, uniformly spaced and have the appropriate irradiance profile for reconstructing the surface slope. This has the advantage of being able to correct for changes in polarized light changes with temperature and aging of the illuminator.

Thermal Impulse Response

In another aspect, the present disclosure provides methods and systems for measuring a thermal impulse response of a tear film of an eye.

Figure 11:
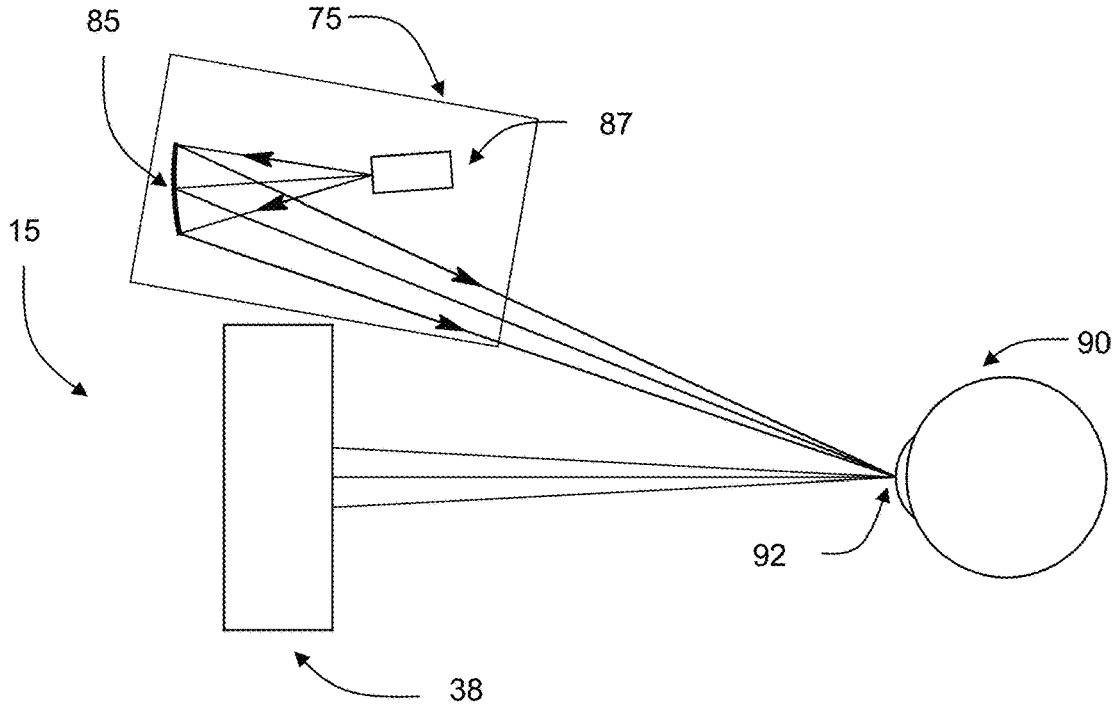
FIG. 11 is a side view of a thermal impulse illuminator and imager.

In another embodiment shown in FIG. 11, an apparatus 15 for measuring thermal impulse response includes an illuminator 75 is configured to be directed toward an eye to irradiate at least a region of the ocular surface with a pattern. This emission is delivered in a pulse having a duration from, for example, 0.1 μs to 1000 μs, inclusive or any value therebetween. In some embodiments, the pulse duration is less than 1 μs. The optical emission has a wavelength that is strongly absorbed by either the tear layer or the cornea so to locally raise the temperature of the region irradiated. For example, the optical emission may increase the temperature of the irradiated region by 0.5° C. to 10° C., inclusive or any other value therebetween. An infrared imager 38 images the ocular surface before and at one or a series of times after the optical emission irradiates a region on the eye. Comparing the temperature of the region on the eye before irradiation and then at one time or multiple times after the irradiation provides information about the tear layer thickness and its response to a minor environmental stress. The image taken before irradiation provides a baseline. The image or images after the irradiation provides information about the thermal decay. The spatial evolution of the temperature distribution provides additional information given that the tear layer is liquid and the cornea is a heterogeneous compound. This difference in material properties influences the spatial redistribution of the absorbed energy.

The thermal diffusion propagation rate is approximately 1 $\mu m/\mu s$ in water. The 1/e absorption depth of 6 $\mu m$ radiation is approximately 3 $\mu m$ in water. This is less than the typical thickness of the tear film. If the tear layer is thicker than 3 $\mu m$ and the pulse width is less than 1-2 $\mu s$, the thermal relaxation will be dominated by properties of the tear film. If the tear layer is thinner than 3 $\mu m$ the thermal relaxation will be dominated by the properties of the cornea.

The emission pattern may be a single spot, a collection of spots, a line or a series of parallel or intersecting lines. The spacing between the lines or spot is large enough so that the irradiated areas do not interact with each other as the temperature distribution after each pulse decays. The width of an irradiated spot or line is between 15 $\mu m$ to 500 $\mu m$. The spacing of the spots or the lines should be greater than 2× the width of the feature size or 30 $\mu m$ to 1 mm. Preferably, the width of the features is one to three times the lateral resolution of the infrared imager 38.

If the frame rate of the thermal camera is slower than the pulse duration, the multiple pulses can be emitted and the time between the pulse and image capture can be varied so to provide temporal resolution of the thermal decay that is finer than frame refresh rate of the thermal camera.

The source of the optical energy can be an electrical filament, a light emitting diode, a laser, or the like. The optical energy from the source may be collected and focused onto the optical surface. FIG. 11 shows an arrangement where an illuminator 75 directs energy to the surface of the eye. In an exemplary embodiment, illuminator 75 comprises a quantum cascade laser 87 emitting at between 10-11 $\mu m$, such as a Thorlabs QD10500CM1-DFB QCL, illuminating an imaging optic 85, which in this embodiment is off-axis ellipsoidal gold-coated mirror. In another exemplary embodiment, a quantum cascade laser 87 emitting at between 6-7 $\mu m$, such as a Thorlabs QD6500CM1-DFB QCL could be used. The laser may be placed at the first focus of the ellipse and the illuminator may be positioned to have the second focus of the ellipse correspond to the ocular surface as well as the object plane for the infrared imager. In such embodiments, the ocular surface may be illuminated by a single spot 92. Assuming the ocular tear film were irradiated by 100 $\mu m$ spot by a 1 $\mu s$ pulse from a laser operating at 6 $\mu m$, the optical energy delivered would be between approximately 0.1 $\mu J$ to 20 $\mu J$. The laser power may be set to be within acceptable ocular laser safety standards for the wavelength used. An example of such a standard is the ANSI Z136 standard.

Figure 12:
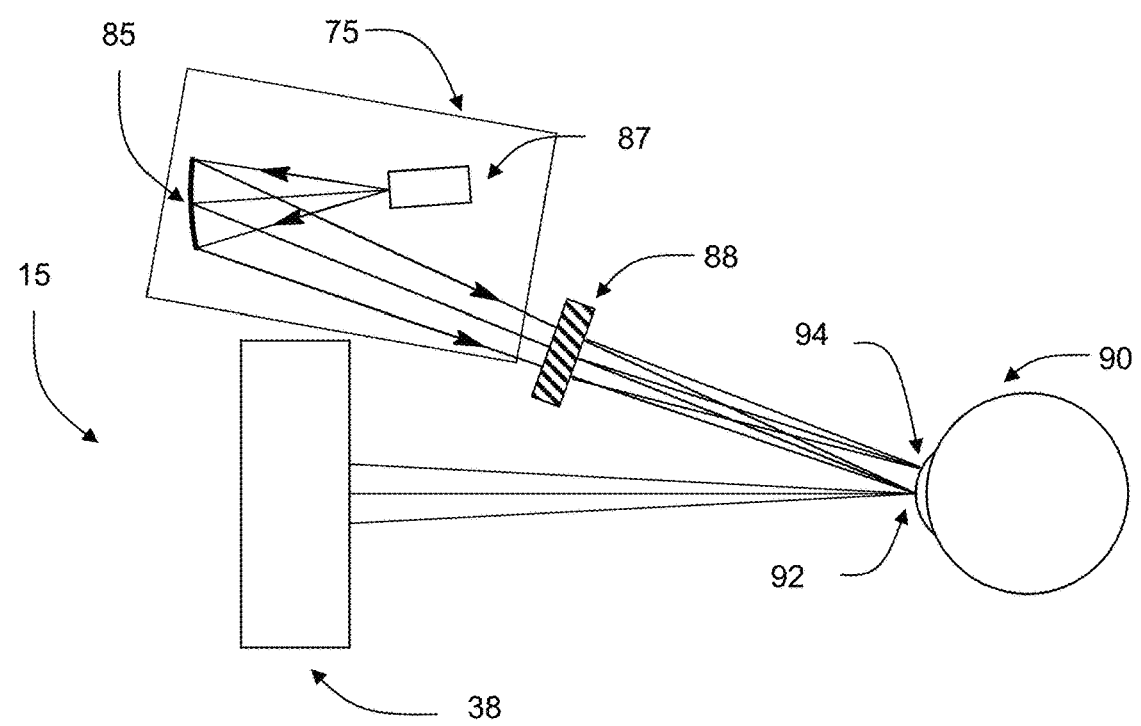
FIG. 12 is a side view of another embodiment of a thermal impulse illuminator and imager.

FIG. 12 shows another embodiment of an illuminator that includes an optical element 88 that redistributes the light from a laser into multiple spots 92 and 94. Optical element 88 may be, for example, a diffraction grating where the distribution of the light from the laser is set by the geometry and spacing of the diffraction features. Optical element 88 can be designed and fabricated to redistribute the light from the laser into an array or spots or lines by diffraction.

Imaging optic 85 could be mounted on an electromechanical mount to steer the illumination pattern to different locations on the eye under the control of controller 40. In this mode, the laser could be run at low power and the position of the pattern could be visualized by the latent thermal emission of the ocular surface. When the laser reaches a point of interest, for example a place on the tear film that appears to thin first after a blink, the laser could be then pulsed to study the thermal pulse behavior of the tear film in that location as a function of time after the onset of the blink.

In another embodiment, a single illumination spot is used, and its position is rastered across the ocular surface as it repeatedly pulses at a range of powers. As the laser power is increased, but remaining within exposure powers that are safe, the deposited energy can stimulate a corneal nerve that will be felt by patient being examined. The location of the stimulus and the amount of energy deposited provide quantitative information about a patient's ocular sensitivity. This information may be important since the symptoms of dry eye do not always correlate to tear film parameters and some patients have either high sensitivity or low sensitivity to corneal stimulus. Mapping corneal sensitivity using this method before and after dry eye treatments could provide useful information on the effectiveness of the therapy.

Figures 7, 8:
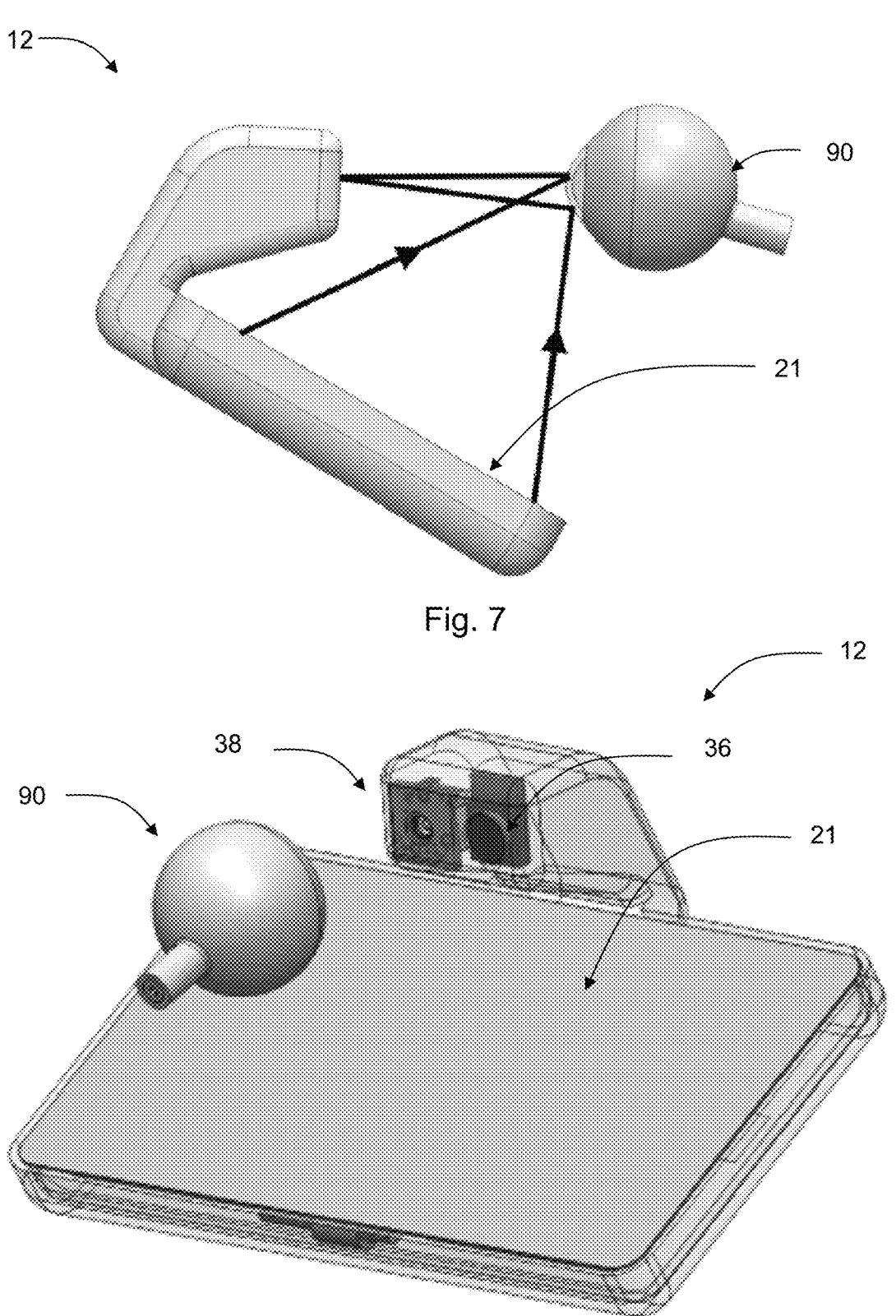
FIG. 7 is a side view of a multimodal imaging system that combines MIE with thermal imaging.
FIG. 8 is an isometric view of a multimodal imaging system that combines MIE with thermal imaging.

In another aspect, thermal imaging can be combined with either ERIE or ARIE. Embodiments of such a system can measure the lipid distribution and correlate it to the dynamic thermal state of the ocular surface. FIG. 7 and FIG. 8 show a side view and isometric view respectively of an integrated MIE and thermal imaging system 12. This system 12 combines a visible-light imager 36 and an infrared imager 38 with a modified LCD (for example, as described above) used as an illuminator 21 to simultaneously or sequentially measure the lipid distribution and correlate it to the dynamic thermal state of the ocular surface. The imager 36 includes imaging optics 24, fixed or adjustable analyzer 34 and imager 30. Visible-light imager 36 has control electronics and a communication interface to set imaging parameters, such as exposure time, pixel binning and analyzer configuration as well as transmit image information for the selected operation mode. As an example, imager 36 can have a fixed analyzer 34 in front of imaging optics 24 that provide a 20° field of view from a 5 megapixel CMOS sensor that provides 10-bit color images over a USB interface.

Infrared imager 38 can use a long-wave infrared camera such as a FLIR™ Lepton infrared imager. Infrared imager can have configurable IR filters to selectively transmit or reflect selected bands of IR light to the thermal sensor. Infrared imager 38 can also have pixels that are configured to detect different bands of IR. Of particular interest are IR bands that have different water absorption, such as 6-9 $\mu m$ and 9-12 $\mu m$. Images from IR bands with different water absorption provide information that can be processed to estimate the thickness of the tear layer. Thus, images from different IR bands with different water absorption can be processed by normalization and subtraction to provide estimated tear thickness maps. Infrared imager 38 has a communication interface such as USB to set imaging parameters including such as exposure time and IR band detected and to communicate the images for the selected operation mode.

Figure 9:
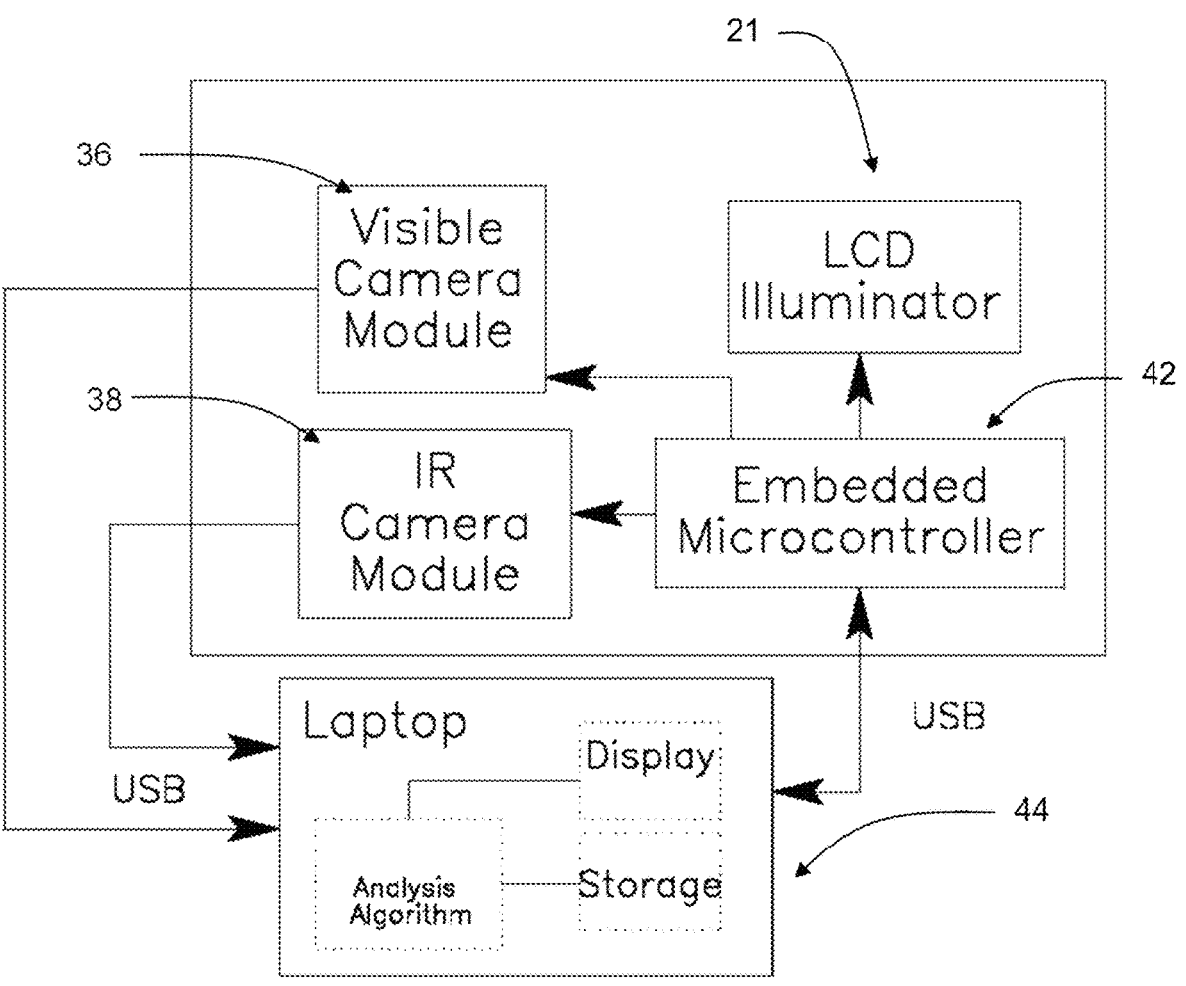
FIG. 9 is a block diagram of the multimodal imaging system that combines MIE with thermal imaging.
Figure 10:
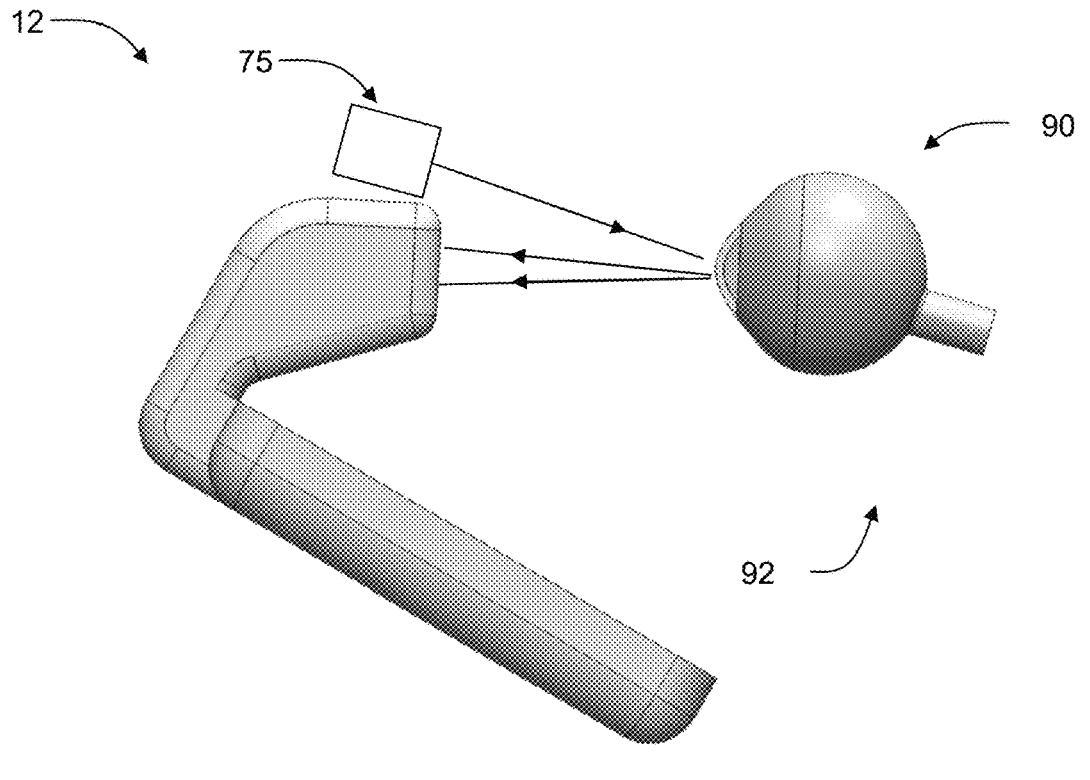
FIG. 10 is a side view of a multimodal imaging system that combines thermal imaging with thermal impulse illumination.

Illuminator 21 is an LED-backlit LCD panel with its front polarizer removed and has a communication interface to adjust the polarization state and brightness of the pixels in the display. Configuring the illuminator is done by writing a predetermined image to the display for each polarized illumination state desired to be associated with a particular image. The system 12 further includes a controller 42 to configure the imager 36, the infrared imager 38, and the illuminator 21. The controller 42 may be configured to store and process images from the system or transmit images from the system 12 to an external controller 44. A block diagram of an exemplary system utilizing an external controller 44 is shown in FIG. 9.

Illuminator 21, visible-light imager 36, and controller 42 alone or in coordination with controller 44 can operate as an ARIE system where images from a phantom 45 are obtained to extract the absolute reflectance of the ocular surface or as an ERIE system where the diversity of illumination polarized states in conjunction with the analyzed state or states allow for the processing of the lipid thickness or lipid index or both.

Exemplary Embodiment

In an exemplary embodiment (similar to that illustrated in FIG. 2), an illuminator utilized white light LEDs located inside a cylinder. A linear polarizer film and a quarter wave film plate were attached to the white LEDs so as to generate left circularly polarized light from these white sources around the inner surface of the cylinder. The light propagates to reach a subject's ocular surface, and the rays are reflected back. Due to the refractive index differences, the reflection is mainly from the interface between tear film's lipid layer and air, a much smaller portion of the reflection is from the lipid-aqueous interface, and an even smaller portion of the reflection is from the aqueous-mucous interface. Other than these foregoing reflections, there are also reflections from the iris. The reflected light passed through two pairs of color corrected doublets, then through a wheel of analyzers, and was ultimately focused on the imager.

Iris color varies from subject to subject, and so does the scattered background light from the iris. In order to get the corneal lipid thickness information, unbiased from the iris background, two orthogonal polarizers may be used in the exemplary tearscope—one immediately attached to the white LEDs, and the other being a rotatory analyzer. Because the rays from the iris are much more likely to go through multiple reflections, they tend to become much more depolarized. Therefore, the polarization state of the reflections from the iris are randomly scattered, while polarization states of the reflections from the lipid-air interface are mainly maintained to be close to left-circularly polarization.

In the exemplary tearscope design, analyzer was a wheel of analyzers contained six different analyzer film plates, and the analyzers were rotating in order. The sequence of the analyzers was left-right-left-right-left-right circular polarizers. When the polarizer and the analyzer are of orthogonal polarization states—i.e., one is left-circularly polarized, and the other right-circularly polarized—then both the reflection upon the cornea and part of the reflection upon the iris will be collected by imaging optics and the imager. This is because the reflection process will flip the polarization to an orthogonal state compared with the incident beam. In contrast, when the polarizer and the analyzer are of the same polarized states, only part of the reflection from the iris will be collected by the imager, since the iris reflection is mostly depolarized.

Before each measurement of a subject, images were obtained of a 7.072 mm radius phantom eye, which was made of SF11 glass type. To minimize the effect of environmental changes inside the test chamber, the glass cornea phantom was imaged prior to and after imaging the subject for later calibration, since the intensity distribution of the white LED illuminators are affected by LED light aging, the temperature and humidity of the ambient environment.

To help with image registration and subject's eye and head movement correction, four blue light LEDs, arranged at the corners of a diamond shape, were attached in the center of the illuminating cylinder adjacent to the entrance pupil. Other colored LEDs can be used. The LEDs used in the exemplary embodiment were non-polarized.

Before analysis of the imaging, the image series was registered for each inter-blink session, which usually lasts for around five seconds. The purpose of registration was to reduce errors induced by movements of the eyes or the head of a subject during the measurement process. Registration was achieved using the four blue LEDs as fiducials. We chose the reference frame as the first frame of the image series in which the eyelid is fully open, and then we aligned the position of the four blue LED reflections shown as blue disks, in all the subsequent images in the ~5-second inter-blink session, to the reference image. Registration is a simple yet critical process for good analysis results, since all the subsequent steps depend on a good registration.

Figure 15:
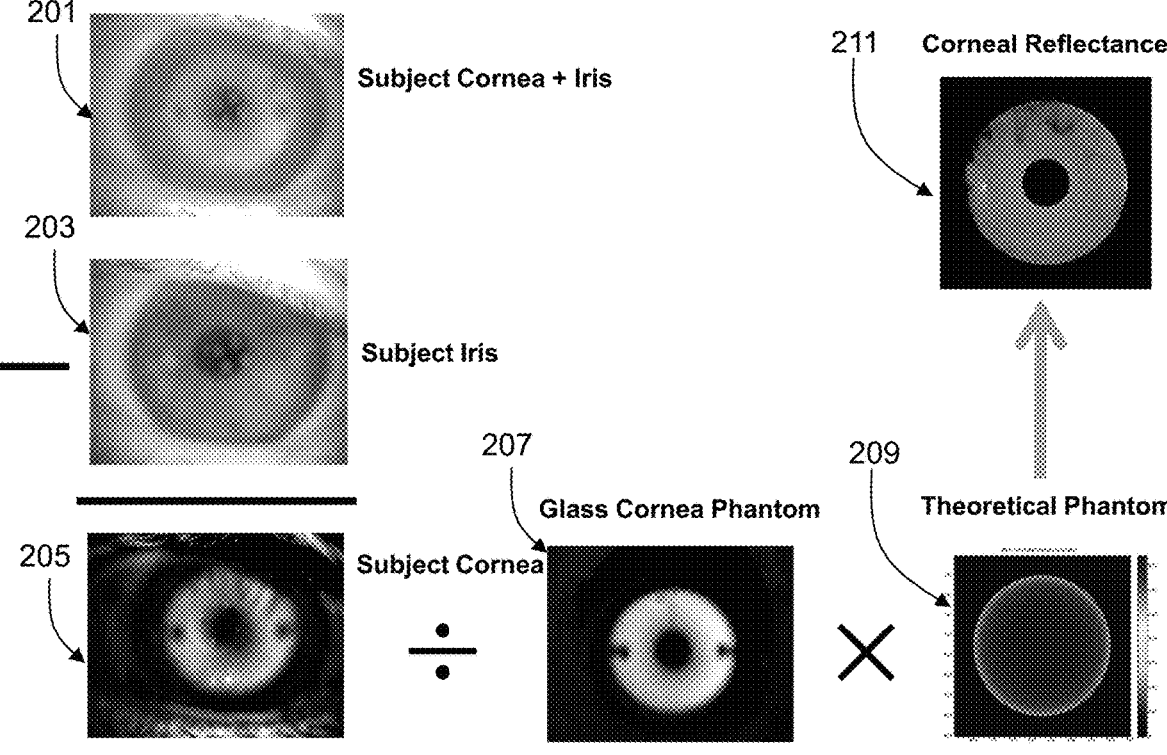
FIG. 15 is a schematic diagram of the analysis of data from an embodiment of an MIE.

After registration, we calculated the corneal reflectance following the schematic diagram shown in FIG. 15. Because we used two orthogonally polarized analyzers sequentially, for each cycle of the wheel of six analyzers, we obtained three bright images (which were images of the subject's cornea and the iris) and three relatively dark images (which were images of the subject's iris only). By subtracting the latter from the former, we obtained an image which was an image of the subject's cornea.

We compared the image of subjects and phantom glass eyes, and resized the phantom images, which were used as reference in the calculation.

We employed Jones calculus to trace the polarization states change with the propagation of the rays. The circularly polarized light were chosen for its symmetry, which simplifies system analysis. The calculation was for the fully polarized components of the light. The depolarization process was taken into account by subtract the dark images from its adjacent bright images.

We computed reflectivity maps for red, green, and blue channels. Reflectivity maps are computed as Measured Subject Ocular Surface×(Theoretical Phantom Ocular Surface/Measured Phantom Ocular Surface). In other words, we divided the subject corneal image with the glass cornea phantom image. We then multiplied the resulting image with the theoretical phantom, thus we obtained the corneal reflectance maps.

Finally, the lipid thickness values for each pixel were calculated from the corneal reflectance maps.

After the original data was processed and analyzed as described above, time course parameters were computed for a crest-shaped region of interest (ROI) positioned on the lower half of the ocular surface as shown in FIG. 14. The shape and size of the ROI were chosen such that the ROI of all subjects had most of the ocular surface free of the upper eye lids when their eyes were open.

Further Discussion

The Jones calculus was used in the data analysis. The general form of the Jones vector analysis is:

$$\vec{E}_{ok} = A\Phi_2 R\Phi_1 \vec{E}_{ik}, \qquad (5)$$

where $\vec{E}_{ik} = [E_{ik_x}, E_{ik_y}]^T$ is the input polarization in the local coordinates of a chief ray, the local coordinates have a latitude and longitude basis, and the point where the chief ray intersects the illuminator is the origin of the local coordinates. $\Phi_1$ is a 2×2 rotation matrix to rotate the input field into the p and s basis in local coordinates on the sample. The p and s components are determined by the intersection of a chief ray leaving the illuminator and specularly reflecting off the sample. The plane of incidence is defined by the chief ray and the surface normal. R is the reflection matrix in the local p and s polarization basis. $\Phi_2$ is a 2×2 rotation matrix to rotate the reflected field from the p and s basis back into the local coordinates of the analyzer, which is a different set of latitude and longitude basis, compared with the illuminator. $\vec{E}_{ok}=[E_{ok_x}, E_{ok_y}]^T$ is the output polarization after the analyzer.

In the exemplary data analysis, the rotation matrices $\Phi_1$ and $\Phi_2$ were ignored. This analysis is correct for portions of the sample that lie at the intersection of either tangential or sagittal imaging plane with the sample because along these intersections, the p and s components directly correspond to the latitudinal and longitudinal components of the illuminator. Including the rotation matrices allows for modeling the electric field reflectivity at other points. For the analysis of points that lie on the intersection of either the tangential or sagittal imaging plane with the sample as shown in the following analysis with Jones calculus, the calculation was simplified to the form of:

$$\vec{E}_{ok}=AR\vec{E}_{ik}, \tag{6}$$

The following discussion starts with the assumption of fully polarized light of illumination. The Jones vector general forms of three different incident beam polarization states are:

$$\vec{E}_{ik} = \begin{bmatrix} a_k \\ b_k e^{i\delta_k} \end{bmatrix}, \tag{7}$$

where $a_k^2+b_k^2=1$, k=1,2,3. The coefficients $a_k$, $b_k$ are all magnitudes of p and s components and are all non-negative real numbers. The input electric fields are normalized, and the absolute electric fields values are ignored. This phase-only modulation was experimentally achieved by using a liquid crystal display (LCD) with the front polarizer removed as further described below. It can also be achieved with other techniques, such as, for example, the use of a spatial light modulator (SLM), or other technique that provides for an area illumination source with spatially controllable output polarization.

When a diffuse (depolarizing) background signal is present, for example, when the iris of the eye is included in the imaging, at least two different input states are used because there are two unknowns to solve—either the index or thickness of the optically thin lipid layer and the diffuse irradiance of the iris image must be considered. If the two input states are polychromatic it is possible to solve for both index and thickness using the spectral variations in detected irradiance. In effective reflectance ellipsometry, at least three different input polarization states are used. In this case, the three different output irradiance can be used to remove the background scattering from the iris and to get two independent tear film reflection data. Four or more different input states would also work. Although additional measurements provide redundancy, the use of such redundant data may improve accuracy. However, each independent polarization measurement takes time, and the lipid layer will evolve, and the eye will move, as the eye is being imaged. Therefore, it is advantageous to minimize the number of measurements and corresponding time required. Two polychromatic measurements represents the minimum number to measure the index and thickness while removing the background signal in absolute reflectance ellipsometry and three measurements are needed in effective reflectance ellipsometry. Minimizing the number of measurements taken also allows for the maximum exposure time for each measurement.

Following the Jones calculus, the reflection matrix is:

$$R = \begin{bmatrix} r_p e^{i\delta_p} & 0 \\ 0 & r_s e^{i\delta_s} \end{bmatrix}, \tag{8}$$

After reflection, the electric field is $$R\vec{E}_{ik} = \begin{bmatrix} a_k r_p e^{i\delta_p} \\ b_k r_s e^{i(\delta_s+\delta_k)} \end{bmatrix} = e^{i\delta_s}\begin{bmatrix} a_k r_p e^{i\Delta} \\ b_k r_s e^{i\delta_k} \end{bmatrix} \tag{9}$$

where $\Delta=\delta_p-\delta_s$.

Since $e^{i\delta_s}$ only adds a constant phase factor to the field, it is dropped in the following analysis.

If a +45° linear polarizer is used as the analyzer, (the direction of the analyzer in the present system is determined from the point of view of the detector), the analyzer matrix is:

$$A = \frac{1}{2}\begin{bmatrix} 1 & 1 \\ 1 & 1 \end{bmatrix}. \tag{10}$$

The output field can be represented as:

$$\vec{E}_{ok} = AR\vec{E}_{ik} = \frac{1}{2}\begin{bmatrix} 1 & 1 \\ 1 & 1 \end{bmatrix}\begin{bmatrix} a_k r_p e^{i\Delta} \\ b_k r_s e^{i\delta_k} \end{bmatrix} = \frac{1}{2}\begin{bmatrix} a_k r_p e^{i\Delta} + b_k r_s e^{i\delta_k} \\ a_k r_p e^{i\Delta} + b_k r_s e^{i\delta_k} \end{bmatrix} \tag{11}$$

The output irradiance values are:

$$I_k = |\vec{E}_{ok}|^2 = \frac{1}{2}|a_k r_p e^{i\Delta} + b_k r_s e^{i\delta_k}|^2 = \frac{1}{2}[a_k^2 r_p^2 + 2a_k b_k r_p r_s \cos(\Delta-\delta_k) + b_k^2 r_s^2] \tag{12}$$

The above equations represent the irradiance values for normalized input fields, which is referred to herein as the "absolute effective reflectance." The constant factor ½ is taken into account if the absolute effective reflectance values are required, such as in the radiometry and photometry photon budget analysis.

The common constant factor ½ may be dropped if only the relative irradiance is considered. Initially, the relative irradiance is used to calculate ellipsometric $\Psi$ and $\Delta$. However, effective reflectance is used to infer index and thickness, the absolute effective reflectance can be retrieved using a phantom reference. Therefore, the above irradiance results can be further simplified as:

$$I_k=|a_k r_p e^{i\Delta}+b_k r_s e^{i\delta_k}|^2=a_k^2 r_p^2+2a_k b_k r_p r_s \cos(\Delta-\delta_k)+b_k^2 r_s^2 \tag{13}$$

Since $I_1$, $I_2$, and $I_3$ are calculated from normalized electric fields inputs, and they represent the part of reflected light that can pass through the analyzer before hitting on the CCD camera, they are referred to herein as "effective reflectance."

Note these effective reflectance values are from the corneal specular reflection, while the irradiance actually reaching the detector will also include the depolarized, diffusely reflected light from the iris. Further, for all the different illumination polarization states, the transmittance values through the cornea are assumed to be approximately the same as for each state and the iris diffuse reflectance values are assumed to be approximately the same. This assumption was experimentally verified. Hence the amount of the iris scattering can be treated as independent of the input polarizations. I' is used to denote the irradiance of both the corneal specular reflection and the iris scattering. Therefore, in total, the irradiance results with each polarization input are:

$$I'_k = I_k + I_{iris} \tag{14}$$

To remove the depolarized light from the iris, effective reflectance values are subtracted off each other, $$I'_2 - I'_1 = I_2 - I_1 = \tag{15}$$
$$(a_2^2 - a_1^2)r_p^2 + 2r_p r_s[a_2 b_2 \cos(\Delta - \delta_2) - a_1 b_1 \cos(\Delta - \delta_1)] + (b_2^2 - b_1^2)r_s^2$$

$$I'_3 - I'_1 = I_3 - I_1 = \tag{16}$$
$$(a_3^2 - a_1^2)r_p^2 + 2r_p r_s[a_3 b_3 \cos(\Delta - \delta_3) - a_1 b_1 \cos(\Delta - \delta_1)] + (b_3^2 - b_1^2)r_s^2$$

$$I'_3 - I'_2 = I_3 - I_2 = \tag{17}$$
$$(a_3^2 - a_2^2)r_p^2 + 2r_p r_s[a_3 b_3 \cos(\Delta - \delta_3) - a_2 b_2 \cos(\Delta - \delta_2)] + (b_3^2 - b_2^2)r_s^2$$

Note that in the above three equations, only two of them are independent. Next, we will rewrite these equations with $\Psi$ and $\Delta$, as common practice in ellipsometry.

From equation (4) above, it is known that $$\rho = \frac{R^p}{R^s} = \tan\Psi e^{i\Delta},$$

and $$\alpha_{ps} = \tan\Psi = \frac{|R_p|}{|R_s|} = \frac{|r_p e^{i\delta_p}|}{|r_s e^{i\delta_s}|} = \frac{|r_p|}{|r_s|}|e^{i\Delta}| = \frac{|r_p|}{|r_s|} = \frac{r_p}{r_s}$$

is defined. Then:

$$\frac{I'_2 - I'_1}{I'_3 - I'_1} = \frac{\begin{array}{c}(a_2^2 - a_1^2)r_p^2 + \\ 2r_p r_s[a_2 b_2 \cos(\Delta - \delta_2) - a_1 b_1 \cos(\Delta - \delta_1)] + \\ (b_2^2 - b_1^2)r_s^2\end{array}}{\begin{array}{c}(a_3^2 - a_1^2)r_p^2 + \\ 2r_p r_s[a_3 b_3 \cos(\Delta - \delta_3) - a_1 b_1 \cos(\Delta - \delta_1)] + \\ (b_3^2 - b_1^2)r_s^2\end{array}} = \tag{18}$$

$$\frac{\begin{array}{c}(a_2^2 - a_1^2)\alpha_{ps}^2 + \\ 2\alpha_{ps}[a_2 b_2 \cos(\Delta - \delta_2) - a_1 b_1 \cos(\Delta - \delta_1)] + \\ (b_2^2 - b_1^2)\end{array}}{\begin{array}{c}(a_3^2 - a_1^2)\alpha_{ps}^2 + \\ 2\alpha_{ps}[a_3 b_3 \cos(\Delta - \delta_3) - a_1 b_1 \cos(\Delta - \delta_1)] + \\ (b_3^2 - b_1^2)\end{array}}$$

Similarly, $$\frac{I'_2 - I'_1}{I'_3 - I'_1} = \frac{\begin{array}{c}(a_2^2 - a_1^2)r_p^2 + \\ 2r_p r_s[a_2 b_2 \cos(\Delta - \delta_2) - a_1 b_1 \cos(\Delta - \delta_1)] + \\ (b_2^2 - b_1^2)r_s^2\end{array}}{\begin{array}{c}(a_3^2 - a_2^2)r_p^2 + \\ 2r_p r_s[a_3 b_3 \cos(\Delta - \delta_3) - a_2 b_2 \cos(\Delta - \delta_2)] + \\ (b_3^2 - b_2^2)r_s^2\end{array}} = \tag{19}$$

$$\frac{\begin{array}{c}(a_2^2 - a_1^2)\alpha_{ps}^2 + \\ 2\alpha_{ps}[a_2 b_2 \cos(\Delta - \delta_2) - a_1 b_1 \cos(\Delta - \delta_1)] + \\ (b_2^2 - b_1^2)\end{array}}{\begin{array}{c}(a_3^2 - a_2^2)\alpha_{ps}^2 + \\ 2\alpha_{ps}[a_3 b_3 \cos(\Delta - \delta_3) - a_2 b_2 \cos(\Delta - \delta_2)] + \\ (b_3^2 - b_2^2)\end{array}}$$

A similar equation for $I'_3 - I'_1/I'_3 - I'_2$ can also be derived, but it would be linearly dependent to the two equations already derived.

Now there are two equations and two unknowns, $\alpha_{ps} = \tan\Psi$, and $\Delta$. Theoretically, by specifying the quadrant, the modulus can be removed, and $\Psi$, and $\Delta$ are obtained, from which the lipid thickness and refractive index can be calculated.

Absolute Reflectance Imaging Ellipsometry (ARIE) and Effective Reflectance Imaging Ellipsometry (ERIE)

The conventional ellipsometry method of using $\Psi$ and $\Delta$ can be sensitive to system noise that limits the accuracy and precision of retrieved the thickness and refractive index. The p and s reflectance amplitude ratio of tan $$\Psi = \frac{|R^p|}{|R^s|} = \frac{r_p}{r_s}$$

is very sensitive to any small structural change in the thin film coating, and this sensitivity is one reason that conventional ellipsometry is able to achieve angstrom-level layer thickness resolution in controlled low-noise conditions. This high sensitivity is an advantage in conventional ellipsometry but extracting layer properties in dynamic systems such as the eye can be an obstacle in cases with large tolerance requirements.

Because of the relatively large tolerance requirements of curved sample and variable eye position for some embodiments of the present MIE, reference measurements of the system were added in order to desensitize the system. It was experimentally determined that retrieving the ratio tan $$\Psi = \frac{r_p}{r_s}$$

alone was not sufficient for systems with large tolerance requirements. The absolute reflectance $r_p$, $r_s$ and the relative phase shift $\Delta$ parameters were calculated simultaneously. To achieve the absolute reflectance measurements, a reference phantom sample with known structure was used to calculate the scaling factors to proportionally relate the irradiance to detector pixel count. A bare BK7 glass phantom was selected as the reference due to its simplicity and environmental robustness: the Fresnel amplitude reflectivity is determined only by the angle of incidence and the indices of the incident (air) and substrate (BK7) materials. Such a phantom can be cleaned without affecting its optical properties. However, other uncoated and coated phantoms may be used. By comparing the effective reflectance off the sample and the bare BK7 phantom reference, the spatial variations in illuminator radiance can be normalized and the $r_p$, $r_s$ and $\Delta$ parameters were retrieved simultaneously. This method is referred to as absolute reflectance imaging ellipsometry (ARIE). For some samples, such as, for example, curved bare substrate samples without a coating, ARIE was proven experimentally to be robust with three different polarization inputs, to retrieve three unknowns: $r_p$, $r_s$, and $\Delta$.

It was also determined that the $r_p$, $r_s$ and $\Delta$ three unknowns need not be retrieved. Rather, the three effective reflectance values of the sample at each pixel can be used, and those values can be compared with the three effective reflectance values of the bare BK7 reference to obtain scaling factors to convert from CCD pixel counts to physical effective reflectance values. For each color channel, which operates at the average wavelength for the color filter and the spectral responsivity of the detector, a specific pair of thickness and index (d, n) will generate a specific set of effective reflectance values ($I_1$, $I_2$, $I_3$), which are three scaled CCD pixel counts at each pixel. By creating a lookup table with all possible thickness and index values within the search range, the measured ($I_1$, $I_2$, $I_3$) can be compared to retrieve the thickness and index (d, n) at each color channel, and retrieve the thickness and refractive index values.

The above concept of using the effective reflectance lookup table to retrieve both the thickness and index is advantageous over previous tearscopes. The current effective reflectance imaging ellipsometry (ERIE) method allows varying both the thickness and the refractive index simultaneously. ARIE and ERIE are explained below.

The CCD pixel counts (PC) are directly proportional to the effective reflectance data. This proportionality is true unless the image is saturated due to long exposure or excessively bright illumination, or when the illumination is extremely low, that the signal to noise ratio is so low that the weak signal is buried in a noisy background. For carefully chosen exposure times, and with pixel binning (if necessary), these two extreme experimental situations can be avoided, and obtain reliable scaling factors.

Therefore, the above results of the mutual subtraction of effective reflectance values can be rewritten as:

$$\frac{PC_2 - PC_1}{m_{21}} = \tag{20}$$
$$(a_2^2 - a_1^2)r_p^2 + 2r_p r_s[a_2 b_2 \cos(\Delta - \delta_2) - a_1 b_1 \cos(\Delta - \delta_1)] + (b_2^2 - b_1^2)r_s^2$$

$$\frac{PC_3 - PC_1}{m_{31}} = \tag{21}$$
$$(a_3^2 - a_1^2)r_p^2 + 2r_p r_s[a_3 b_3 \cos(\Delta - \delta_3) - a_1 b_1 \cos(\Delta - \delta_1)] + (b_3^2 - b_1^2)r_s^2$$

$$\frac{PC_3 - PC_2}{m_{32}} = \tag{22}$$
$$(a_3^2 - a_2^2)r_p^2 + 2r_p r_s[a_3 b_3 \cos(\Delta - \delta_3) - a_2 b_2 \cos(\Delta - \delta_2)] + (b_3^2 - b_2^2)r_s^2$$

In the above equations, the $PC_1$, $PC_2$, and $PC_3$ are experimentally measured pixel counts for each color channel of three different polarization incidence. $m_{21}$, $m_{31}$, and $m_{32}$ are three scaling factors which are measured from phantom glass samples to calibrate the system. Therefore, the only unknowns are $r_p$, $r_s$, and $\Delta$. With three unknowns and three equations, $r_p$, $r_s$, and $\Delta$ can be simultaneously using ARIE.

If ERIE is used, there is no need to solve $r_p$, $r_s$, and $\Delta$, but rather, the three scaled pixel counts subtraction values $(PC_2-PC_1)/m_{21}$, $(PC_3-PC_1)/m_{31}$, and $(PC_3-PC_2)/m_{32}$ can be directly compared with a lookup table of all possible thickness and index within a chosen search range based on predetermined knowledge of the sample.

The scaling factors between the pixel counts and the reflectance can be calibrated with a glass phantom with known structure experimentally. The method to calibrate uses the same equations above, but with a known phantom structure such as bare BK7, so that $r_p$, $r_s$, and $\Delta$ are known for the phantom samples. $PC_1$, $PC_2$, and $PC_3$, or their subtraction from each other, will be measured and scaling factors calculated from these measured values.

$$m_{21} = \left\{ \frac{PC_2 - PC_1}{r_p^2(a_2^2 - a_1^2) + r_s^2(b_2^2 - b_1^2) + 2r_p r_s[a_2 b_2 \cos(\Delta - \delta_2) - a_1 b_1 \cos(\Delta - \delta_1)]} \right\}_{ph} \tag{23}$$

$$m_{31} = \left\{ \frac{PC_3 - PC_1}{r_p^2(a_3^2 - a_1^2) + r_s^2(b_3^2 - b_1^2) + 2r_p r_s[a_3 b_3 \cos(\Delta - \delta_3) - a_1 b_1 \cos(\Delta - \delta_1)]} \right\}_{ph} \tag{24}$$

$$m_{32} = \left\{ \frac{PC_3 - PC_2}{r_p^2(a_3^2 - a_2^2) + r_s^2(b_3^2 - b_2^2) + 2r_p r_s[a_3 b_3 \cos(\Delta - \delta_3) - a_2 b_2 \cos(\Delta - \delta_2)]} \right\}_{ph} \tag{25}$$

where "ph" stands for phantom.

Above, the input light was assumed to be fully polarized. But even if there is some degree of depolarization in the input light, as long as the degrees of depolarization are similar for the three input states, or in other words, as long as the depolarized light irradiance are consistent for the three input polarizations, the above calculation is still accurate. This is because in the process of subtracting the effective irradiance values from each other, not only is the depolarized light scattered from the iris removed, but also the depolarized light contribution is subtracted from the original light input. In testing an experimental setup, it was found that the input light from a modified LCD is sufficiently close to fully polarized light, and the degree of depolarization of the input illumination of different polarization states are sufficiently close, hence could be subtracted off each other.

Although the present disclosure has been described with respect to one or more particular embodiments, it will be understood that other embodiments of the present disclosure may be made without departing from the spirit and scope of the present disclosure.

We claim:

1. An apparatus for measuring thermal impulse response of a tear film of an eye, comprising:
an infrared source configured to emit infrared energy and heat the tear film according to a known spatial pattern;
an infrared imager configured to receive infrared energy emitted by the eye; and
a controller configured to:
pulse the infrared source to emit infrared energy for a period of time;
obtain from the infrared imager, at least one infrared image of at least a portion of the eye at a predetermined time after the pulse, wherein the imaged portion of the eye includes an infrared signal resulting from the spatial pattern of the heated tear film;
analyze a thermal decay of the infrared signal following the pulse to determine a thermal impulse response of the tear film; and determine a thickness of the tear film of the eye based on the thermal impulse response.

2. The apparatus of claim 1, wherein the infrared source comprises a mask for creating the spatial pattern.

3. The apparatus of claim 1, wherein the spatial pattern is a slit.

4. The apparatus of claim 1, wherein the spatial pattern is a plurality of dots.

5. The apparatus of claim 1, further comprising an optical assembly for focusing the spatial pattern of infrared energy onto the tear film of the eye.

6. The apparatus of claim 1, wherein the infrared source is configured to emit long-wave and/or mid-wave infrared energy.

7. The apparatus of claim 1, wherein the infrared source comprises a bandpass filter.

8. The apparatus of claim 1, further comprising a user interface configured to receive an indication from a patient as to whether the patient perceived a localized thermal stimulus; and wherein the controller is further configured to:

correlate an indication received via the user interface to a location of thermal stimulus based on the known spatial pattern; and generate a corneal sensitivity map of the eye based on received indications from the patient to a plurality of localized thermal stimuli.

9. The apparatus of claim 1, wherein the first thermal image is of thermal energy in a first band; and wherein the controller is further configured to:

obtain from the infrared imager, a second thermal image containing at least a portion of the eye, wherein the second thermal image is of thermal energy in a second band different from the first band; and determine an estimated tear film thickness based on the first thermal image and the second thermal image.

* * * * *